(12) United States Patent
Perrier

(10) Patent No.: US 10,509,012 B2
(45) Date of Patent: *Dec. 17, 2019

(54) SOUND PROPAGATION COMPARISON WITH AUTOMATED FREQUENCY SELECTION FOR PIPE CONDITION ASSESSMENT

(71) Applicant: Mueller International, LLC, Atlanta, GA (US)

(72) Inventor: Sebastien Perrier, Toronto (CA)

(73) Assignee: Mueller International, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/232,268

(22) Filed: Dec. 26, 2018

(65) Prior Publication Data

US 2019/0128848 A1 May 2, 2019

Related U.S. Application Data

(63) Continuation of application No. 15/493,899, filed on Apr. 21, 2017, now Pat. No. 10,209,225.

(51) Int. Cl.
*G01M 3/24* (2006.01)
*G01M 3/00* (2006.01)
(Continued)

(52) U.S. Cl.
CPC .............. *G01N 29/07* (2013.01); *G01M 3/00* (2013.01); *G01M 3/243* (2013.01); *G01N 29/043* (2013.01); *G01N 2291/0289* (2013.01)

(58) Field of Classification Search
CPC ...... G01M 3/00; G01M 3/243; G01N 29/043; G01N 29/07; G01N 2291/0289
(Continued)

(56) References Cited

U.S. PATENT DOCUMENTS 4,289,019 A 9/1981 Claytor
5,416,724 A 5/1995 Savic
(Continued)

FOREIGN PATENT DOCUMENTS

CN 106289121 1/2017
EP 3392636 10/2018
WO 2014050618 4/2014

OTHER PUBLICATIONS

Perrier, Sebastien; Issue Notification for U.S. Appl. No. 15/493,899, filed Apr. 21, 2017, dated Jan. 30, 2019, 1 pg.
(Continued)

*Primary Examiner* — Jacques M Saint Surin
(74) *Attorney, Agent, or Firm* — Taylor English Duma LLP

(57) ABSTRACT

Examples of collecting and analyzing acoustic data for condition assessment within a fluid distribution system are disclosed. In one example implementation according to aspects of the present disclosure, a method for collecting and analyzing acoustic data for condition assessment within a fluid distribution system includes: receiving pipe segment criteria for a pipe segment, the pipe segment including a length of a pipe between a first computing node and a second computing node; determining a predicted parameter based on the received pipe segment criteria for the pipe segment; utilizing the predicted parameter to measure an actual speed of sound for the pipe segment between the first computing node and the second computing node; and comparing the actual speed of sound and a theoretical speed of sound to calculate a predicted pipe degradation for the pipe segment.

20 Claims, 17 Drawing Sheets

(51) Int. Cl.
*G01N 29/04* (2006.01)
*G01N 29/07* (2006.01)

(58) Field of Classification Search
USPC .......................................................... 73/592
See application file for complete search history.

(56) References Cited

U.S. PATENT DOCUMENTS

| | | | |
|---|---|---|---|
| 5,531,099 | A | 7/1996 | Russo |
| 6,435,030 | B1 | 8/2002 | Gysling |
| 6,453,247 | B1 | 9/2002 | Hunaidi |
| 7,007,545 | B1 | 3/2006 | Martinek |
| 7,203,322 | B1 | 4/2007 | Bostock |
| 7,328,618 | B2 * | 2/2008 | Hunaidi ................. G01B 17/02 73/597 |
| 7,810,378 | B2 * | 10/2010 | Hunaidi ................. G01M 3/243 73/40.5 A |
| 8,601,875 | B2 * | 12/2013 | Paulson ............... G01N 29/043 73/598 |
| 9,053,519 | B2 | 6/2015 | Scolnicov |
| 10,209,225 | B2 | 2/2019 | Perrier |
| 2005/0000289 | A1 | 1/2005 | Gysling et al. |
| 2006/0283251 | A1 | 12/2006 | Hunaidi |
| 2008/0078247 | A1 | 4/2008 | Hunaidi |
| 2008/0314122 | A1 | 12/2008 | Hunaidi |
| 2009/0250125 | A1 | 10/2009 | Howitt |
| 2011/0161037 | A1 | 6/2011 | Sutherland |
| 2012/0041694 | A1 | 2/2012 | Stephens et al. |
| 2012/0055262 | A1 * | 3/2012 | Sinha ..................... G01F 1/66 73/861.04 |
| 2013/0211797 | A1 | 8/2013 | Scolnicov |
| 2013/0213482 | A1 | 8/2013 | Schuberth |
| 2015/0300907 | A1 | 10/2015 | Giunta |
| 2016/0041286 | A1 * | 2/2016 | Sinha ..................... G01F 1/667 73/152.32 |
| 2016/0252422 | A1 | 9/2016 | Howitt, IV |
| 2016/0290974 | A1 | 10/2016 | Coleman |
| 2016/0370325 | A1 | 12/2016 | Yusuf |
| 2018/0306753 | A1 | 10/2018 | Perrier |
| 2018/0306755 | A1 * | 10/2018 | Perrier ................... G01M 3/00 |
| 2018/0308265 | A1 | 10/2018 | Perrier et al. |
| 2019/0128766 | A1 * | 5/2019 | Burtea ................. G01M 3/243 |
| 2019/0128767 | A1 * | 5/2019 | Burtea ................. G01M 3/243 |

OTHER PUBLICATIONS

Perrier, Sebastien; Notice of Allowance for U.S. Appl. No. 15/493,899, filed Apr. 21, 2017, dated Sep. 24, 2018, 13 pgs.

Perrier, Sebastien; Supplemental Notice of Allowance for U.S. Appl. No. 15/493,899, filed Apr. 21, 2017, dated Nov. 9, 2018, 6 pgs.

Leinov et al., "Investigation of guided wave propagation and attenuation in pipe buried in sand", J of Sound and Vibration 347 (2015) 96-114.

Long et al., "The effect of soil properties on acoustic wave propagation in buried iron water pipes", AIP Conference Proceedings 615, 1310 (2002).

Perrier, Sebastien; Non-Final Office Action for U.S. Appl. No. 15/493,914, filed Apr. 21, 2017, dated Dec. 14, 2018, 19 pgs.

Perrier, Sebastien; Extended European Search Report for serial No. 18166849.2, filed Apr. 11, 2018, dated Jul. 19, 2018, 7 pgs.

Almeida, et al.; Article entitled: "On the Acoustic Filtering of the Pipe and Sensor in a Buried Plastic Water Pipe and its Effect on Leak Detection: An Experimental Investigation", Sensors, published on Mar. 20, 2014, 16 pgs.

De Almeida, et al.; Article entitled: "Measurement of Wave Attenuation in Buried Plastic Water Distribution Pipes", Journal of Mechanical Engineering, published on Apr. 1, 2014, 9 pgs.

Oelze, et al.; Article entitled: "Measurement of Attenuation and Speed of Sound in Soils", Soil Sci. Soc. Am. J., vol. 66, May-Jun. 2002, 9 pgs.

Perrier, Sebastien; Ex Parte Quayle Action for U.S. Appl. No. 15/493,914, filed Apr. 21, 2017, mailed Jun. 13, 2019, 15 pgs.

Perrier, Sebastien; Non-Final Office Action for U.S. Appl. No. 15/493,906, filed Apr. 21, 2017, dated Jul. 5, 2019, 22 pgs.

Perrier, Sebastien; Notice of Allowance for U.S. Appl. No. 15/493,906, filed Apr. 21, 2017, dated Oct. 2, 2019, 11 pgs.

Perrier, Office Action for European for serial No. 18166849.2, filed Apr. 11, 2018, dated Sep. 19, 2019, 5 pgs.

* cited by examiner

FIG. 8

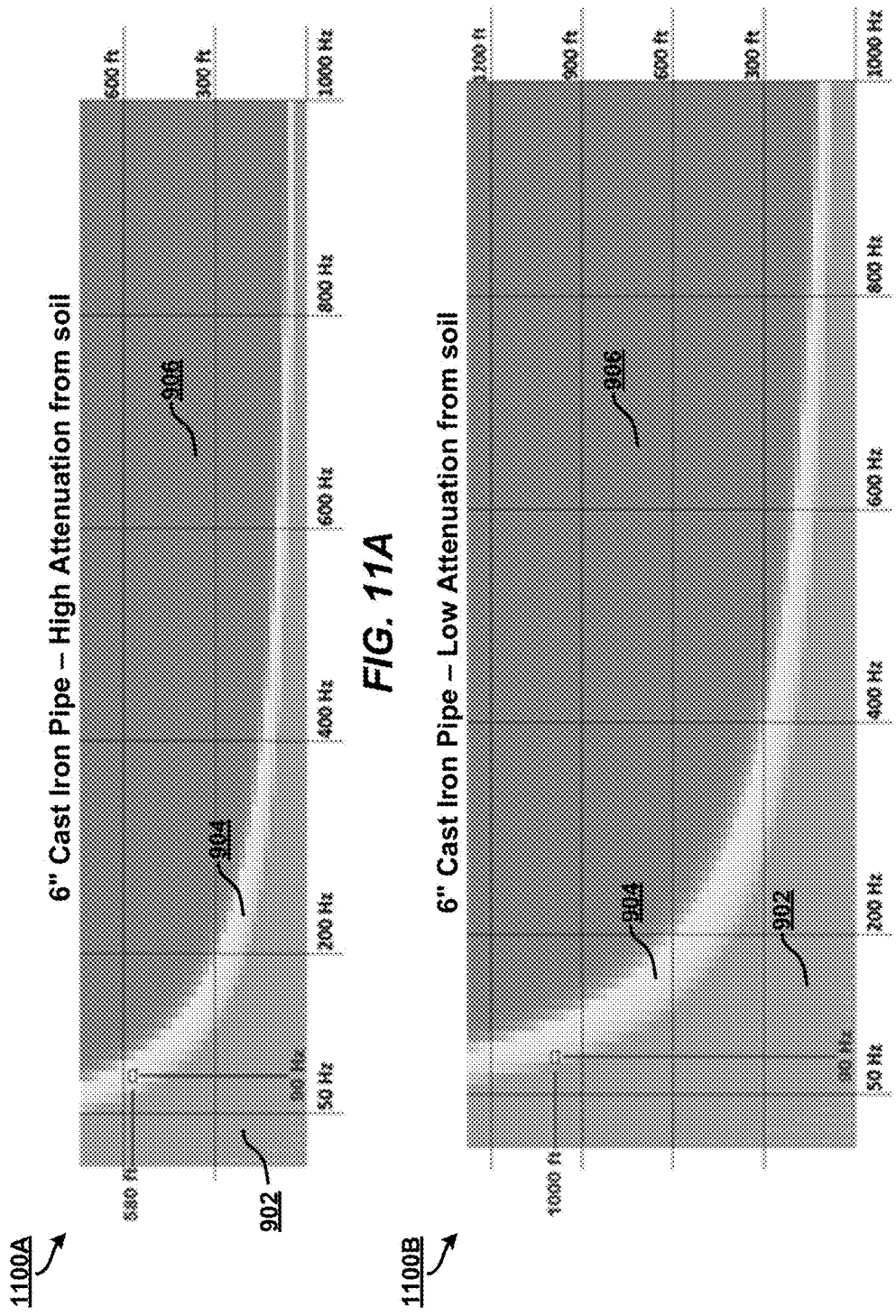

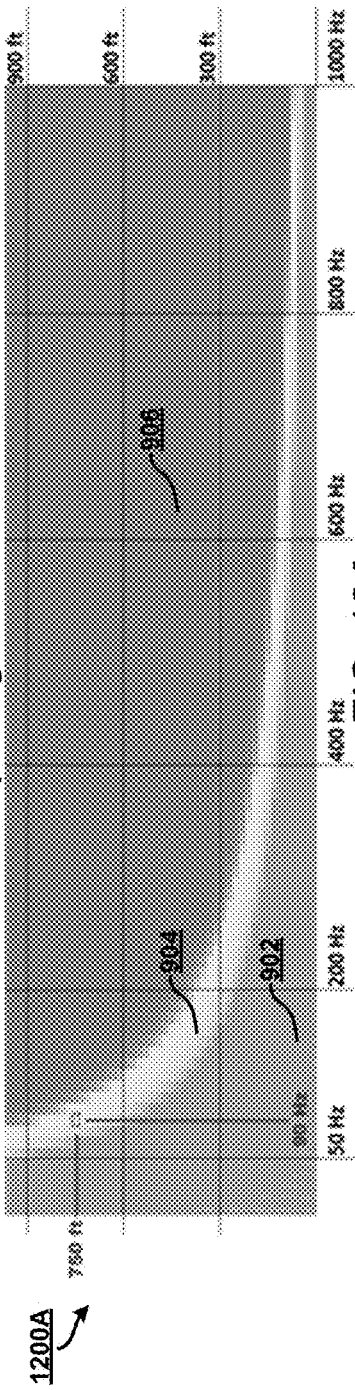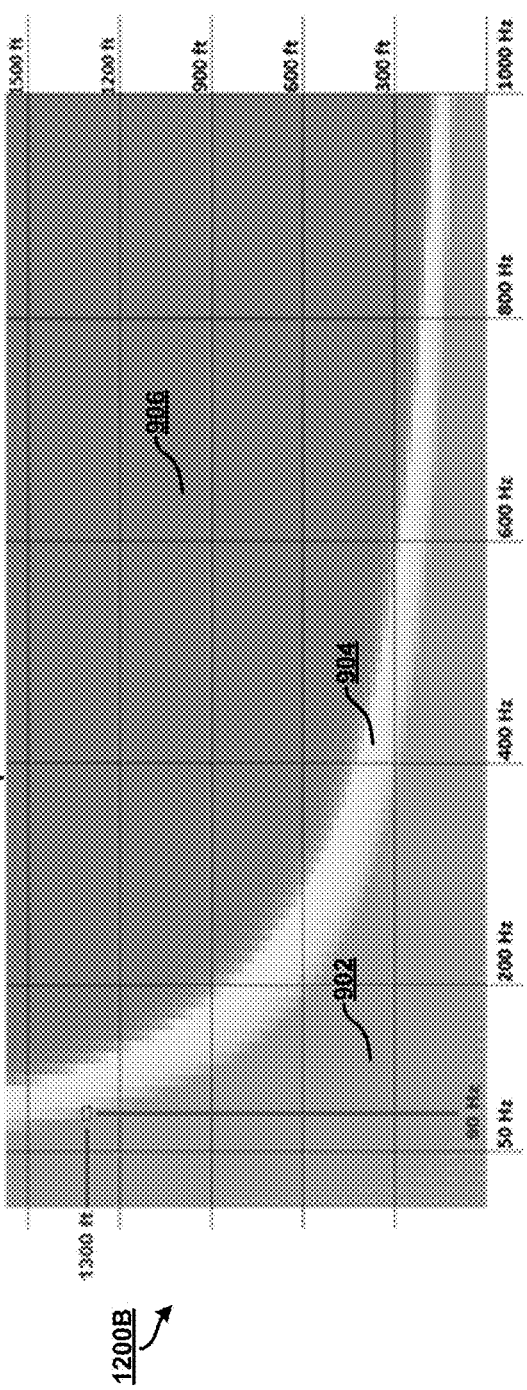

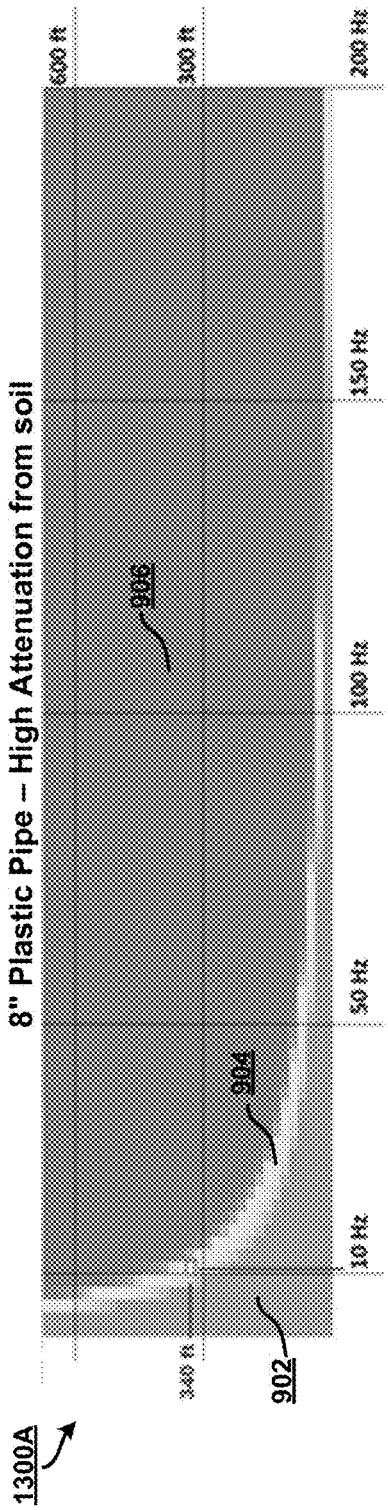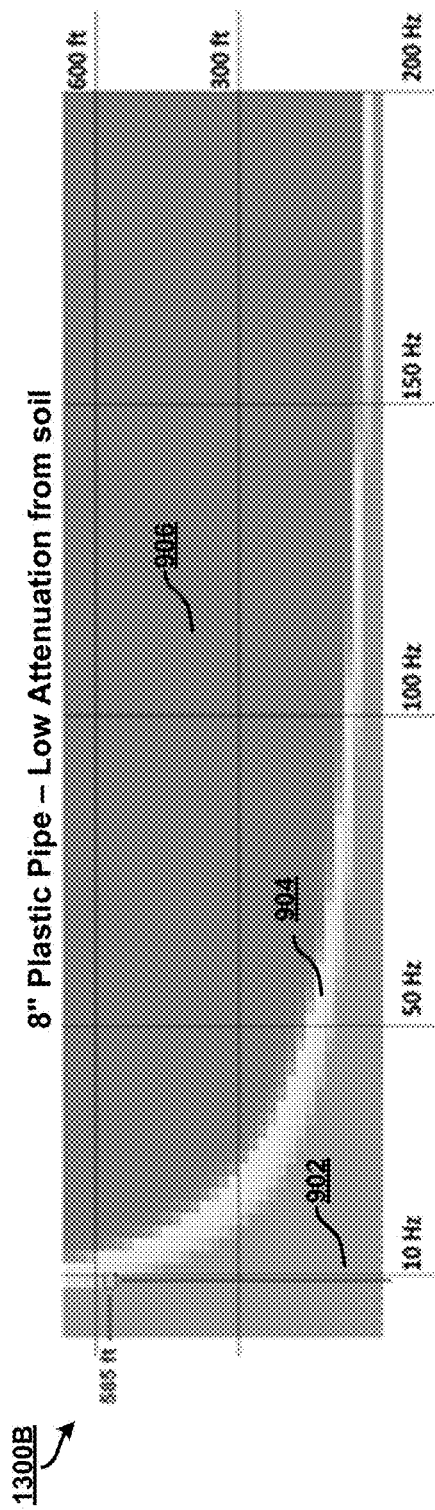

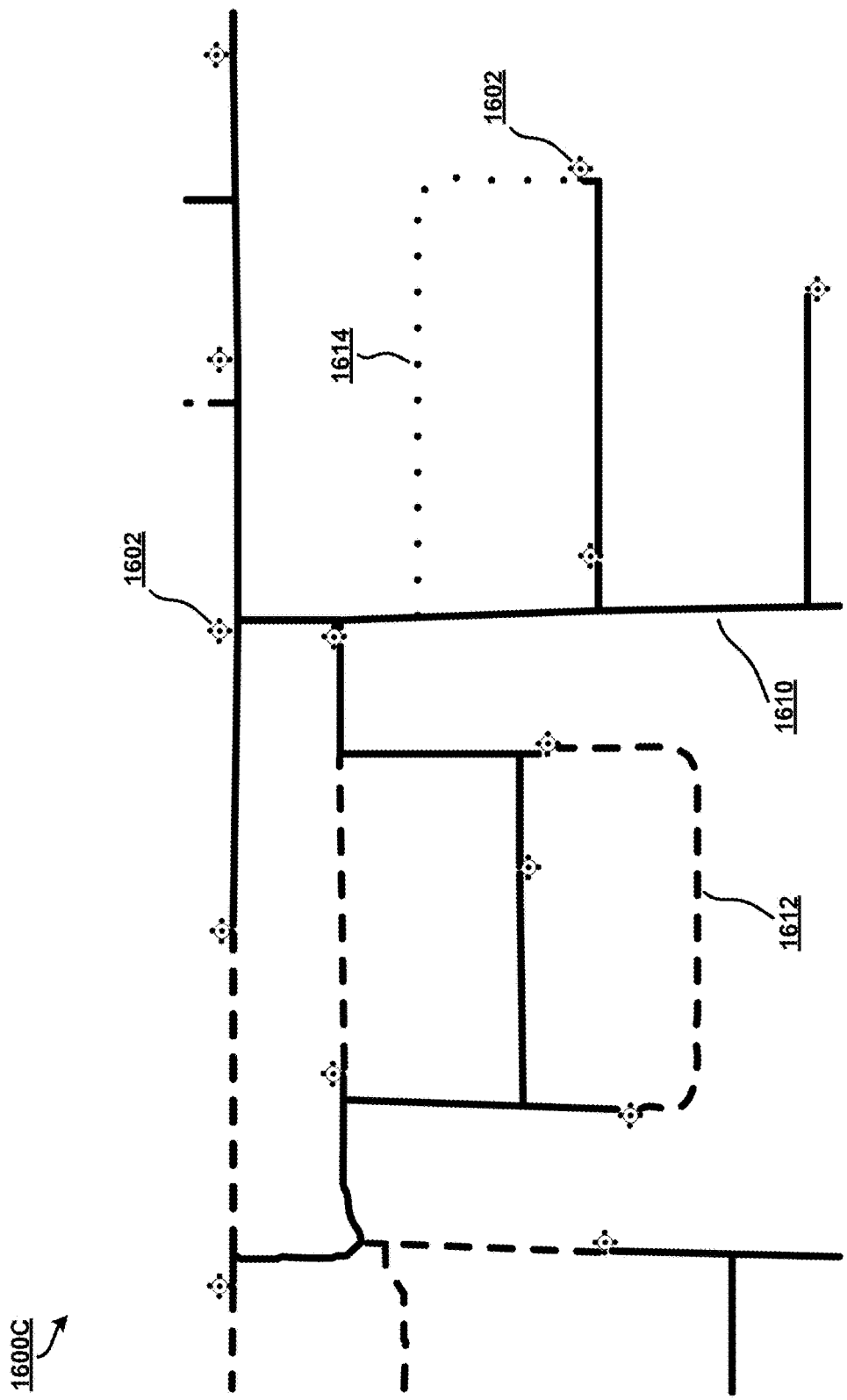

SOUND PROPAGATION COMPARISON WITH AUTOMATED FREQUENCY SELECTION FOR PIPE CONDITION ASSESSMENT

CROSS-REFERENCE TO RELATED APPLICATION

This application is a continuation of U.S. application Ser. No. 15/493,899, filed Apr. 21, 2017, which is hereby incorporated by reference herein in its entirety.

BACKGROUND

A utility provider may install and maintain infrastructure to provide utility services to its customers. For example, a water utility provider may implement a fluid distribution system to distribute water to its customers. Metering devices may be utilized by the utility provider to determine consumption of the provided utility (e.g., water, electricity, gas, etc.). The utility provider may implement various devices or computing nodes throughout the fluid distribution system to monitor the status of the fluid distribution system, including condition assessment for the pipes used therein, predicting attenuation based on type of pipe and type of surrounding soil, and graphically mapping efficient layouts of the computing node locations based on propagating distances.

Due to the rapidly escalating costs of potable water, the scarcity of fresh water supplies, the increasing costs for water treatment and distribution, and the potential for costly damage to subsurface infrastructure, accurate condition assessment and minimizing leaks in water distribution systems is a goal of both public and private water distribution utilities. If a leak is not particularly conspicuous, it may go undetected for months at a time without repair. It is therefore important to be able to assess pipe degradation early before leaks.

Several techniques for condition assessment currently exist for direct condition assessment, including visual inspection, leak detection systems, wall thickness measurements, soil testing, corrosion monitoring, and analyzing break history in similar pipes in the network of water pipes. Leak detection systems utilizing acoustic monitoring can also be used to perform condition assessment by providing an indication of average wall thickness between two measuring points. These acoustic monitoring systems are good screening tools for detecting widespread corrosion and wall loss, they are non-intrusive, and generally are low cost. However, current techniques utilizing acoustic monitoring are not reliable and may still require unnecessary and costly visual inspection. There is therefore a need for a condition assessment system that accurately determines condition assessment in a network of water pipes without having to rely on visual inspection. Furthermore, there is also a need that enables reliable placement for computing nodes for a fluid distribution system by utilizing graphical mapping and acoustical understanding of sound propagation in the pipe network.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

The present disclosure relates to collecting and analyzing data in a fluid distribution system to determine pipe degradation based on loss from the pipe wall thickness. According to some aspects, a method for receiving and analyzing data for condition assessment within a fluid distribution system comprises receiving pipe segment criteria for a pipe segment. The pipe segment comprises a length of a pipe between a first computing node and a second computing node. A predicted parameter based on the received pipe segment criteria for the pipe segment is determined, and that predicated parameter is then utilized to measure an actual speed of sound for the pipe segment between the first computing node and the second computing node. Finally, the method comprises comparing the actual speed of sound and a theoretical speed of sound to calculate a predicted pipe degradation for the pipe segment.

According to further aspects, a system for collecting and analyzing acoustic data for condition assessment within a fluid distribution system comprises a plurality of computing nodes and a computing host in communication with the plurality of computing nodes. The plurality of computing nodes are in communication with the fluid distribution system and configured to acquire acoustic data in the fluid distribution system. The computing host is programmed to perform steps. The first step comprises receiving pipe segment criteria for a pipe segment. The pipe segment comprises a length of a pipe between a first computing node and a second computing node. A predicted parameter based on the received pipe segment criteria for the pipe segment is determined, and that predicated parameter is then utilized to measure an actual speed of sound for the pipe segment between the first computing node and the second computing node. Finally, the last step the computing host is programmed to perform is comparing the actual speed of sound and a theoretical speed of sound to calculate a predicted pipe degradation for the pipe segment.

According to further aspects, a non-transitory computer-readable storage medium storing instructions that, when executed by a processing resource, cause the processing resource to perform steps. The first step comprises receiving pipe segment criteria for a pipe segment. The pipe segment comprises a length of a pipe between a first computing node and a second computing node. A predicted parameter based on the received pipe segment criteria for the pipe segment is determined, and that predicated parameter is then utilized to measure an actual speed of sound for the pipe segment between the first computing node and the second computing node. Finally, the last step comprises comparing the actual speed of sound and a theoretical speed of sound to calculate a predicted pipe degradation for the pipe segment.

These and other features and aspects of the various aspects will become apparent upon reading the following Detailed Description and reviewing the accompanying drawings. Furthermore, other examples are described in the present disclosure. It should be understood that the features of the disclosed examples can be combined in various combinations. It should also be understood that certain features can be omitted while other features can be added.

BRIEF DESCRIPTION OF THE DRAWINGS

In the following Detailed Description, references are made to the accompanying drawings that form a part hereof, and that show, by way of illustration, specific aspects or examples. Any illustrated connection pathways in block and/or circuit diagrams are provided for purposes of illustration and not of limitation, and some components and/or interconnections may be omitted for purposes of clarity. The drawings herein are not drawn to scale. Like numerals represent like elements throughout the several figures.

FIG. 8 illustrates a screen diagram of a user interface to analyze data collected within a fluid distribution system and determine pipe degradation utilizing predicted frequency content according to examples of the present disclosure.

FIGS. 11A-11B illustrate example colormaps relating to the techniques for collecting and analyzing data to generate and utilize pipe-specific sound attenuation ranges within a fluid distribution system according to examples of the present disclosure.

FIGS. 12A-12B illustrate example colormaps relating to the techniques for collecting and analyzing data to generate and utilize pipe-specific sound attenuation ranges within a fluid distribution system according to examples of the present disclosure.

FIG. 13A-13B illustrate example colormaps relating to the techniques for collecting and analyzing data to generate and utilize pipe-specific sound attenuation ranges within a fluid distribution system according to examples of the present disclosure.

FIGS. 16A-16C illustrate a diagram of a fluid distribution system with computing nodes for collecting and analyzing acoustic data for graphical mapping of computing node location selection within the fluid distribution system according to examples of the present disclosure.

DETAILED DESCRIPTION

Figure 1:
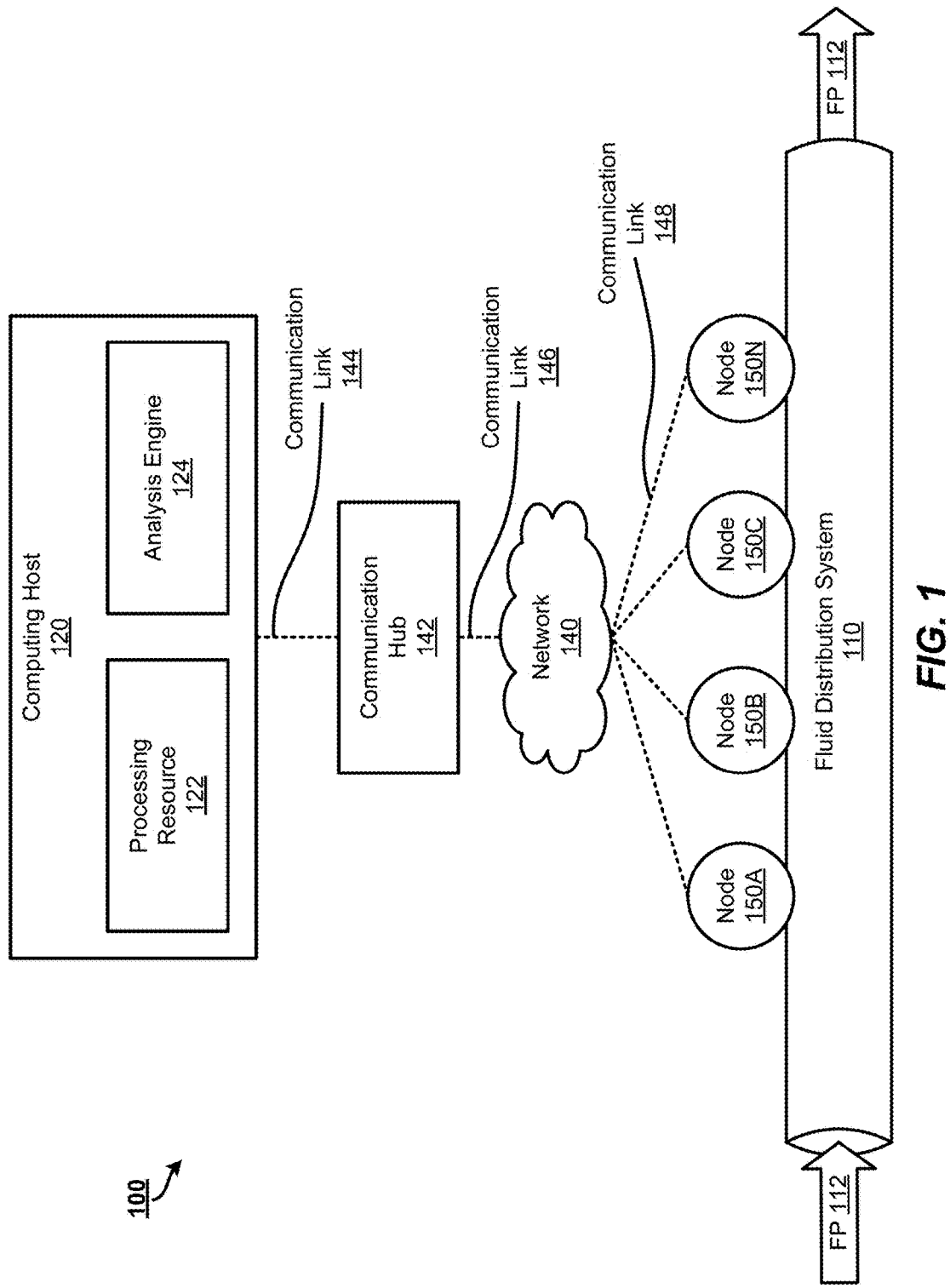
FIG. 1 illustrates a diagram of an environment to collect and analyze acoustic data for condition assessment and leak detection within a fluid distribution system according to examples of the present disclosure.

Various implementations are described below by referring to several examples of collecting and analyzing acoustic data in a fluid distribution system. In examples, the water utility provider may deploy devices (nodes) across the fluid distribution system to collect data relating to the network of pipes. The data may then be analyzed to determine pipe degradation based on loss from the pipe wall thickness, predict pipe attenuation based on the type of pipe and soil type, or determine efficient node location utilizing graphical mapping. Other example implementations and variations are disclosed herein.

The present disclosure enables reliable condition assessment for a fluid distribution system by utilizing sound propagation comparison with automated frequency selection. In acoustics, from a theoretical perspective, the frequency content of cylindrical waveguides is relatively known and is dependent on several parameters. Water pipes may be considered as cylindrical waveguides; therefore, their fundamental frequency content for acoustic propagation may be predicted using parameters such as the diameter, the thickness of the wall, the distance of propagation, the attenuation of the pipe material, and so forth. In real water networks, pipes depict a vibro-acoustical behavior which is not just that of cylindrical waveguides. Certain conditions tend to modify the vibro-acoustic behavior of pipes (pipe supports, local stiffeners, pipe junctions, etc.). These changes, induced in the vibro-acoustic behavior of the pipes, make the analysis of sound files more complicated. When analyzing the behavior of pipes using their frequency content, errors can be present in the results due to the modifications in behavior explained before. Thus, selecting the wrong frequency content will lead to incorrect results and wrong predictions. To avoid these mistakes in interpreting the frequency content of corrupted sound files, the present disclosure considers the pipe as a perfect cylindrical waveguide and uses the equivalent theoretical frequency content for analysis.

According to aspects described herein, an acoustical model utilizing specific parameters such as the pipe diameter, the wall thickness, the material and its mechanical characteristics, the distance between sensors (nodes), and the attenuation to predict the frequency content of measurement between acoustical sensors may be used. According to further aspects described herein, the acoustical model may be simplified as a mathematical formula which can predict a range of frequency.

The present disclosure further enables reliable detection for predicting a more precise distance a leak noise will propagate within a pipe network. Once a leak forms in a water network, a noise can be detected in the proximity of the leak. How far from the leak location this noise can be detected is valuable information for water distribution utilities. It is known that the noise generated by a leak is dependent on multiple parameters such as the leak size, the pressure, the pipe specific dimensions and material, the attenuation from the soil, and the like. However, no model allows to predict the sound level generated by a specific leak. Therefore, it is difficult to predict the exact distance a leak noise will propagate within a pipe network. The present disclosure describes a more reliable method to evaluate and predict a more precise distance a noise will propagate in a specific pipe.

According to aspects described herein, the distance the noise generated by a leak may propagate in a water network may be dependent on multiple parameters including elements specific to the pipe networks, and statistical parameters obtained with measurement on various sites. According to aspects described herein, utilizing a combination of parameters specific to the pipe, parameters from literature review, e.g. research articles, to take into account the soil attenuation, and parameters from measurement on various sites, a statistically possible leak noise measured by a sound level may be determined. According to aspects described herein, a mathematical formula may be used that integrates several parameters, either entered by a user or predefined in the system, into a computing host to present the distance a leak noise may propagate for a specific type of pipe. According to aspects described herein, a range of distance for possible propagation along with the frequency dependent acoustical attenuation may be calculated and displayed as a colormap. According to aspects described herein, a colormap may allow more precise prediction of the frequency of propagation and the distance the noise should propagate for different type of pipes and soil configurations.

The present disclosure further enables reliable placement for computing nodes for a fluid distribution system by utilizing graphical mapping and acoustical understanding of sound propagation in the pipe network. The installation of an acoustic propagation detection system, such as the Echologics EchoShore-DX system, necessitates the installation of computing nodes on hydrants, or other components of the pipe network, to create a network of acoustical sensors to detect leaks. Determining which hydrant should receive a computing node requires several hours of manual work, and the operator would have to look at a map to select the hydrants where computing nodes should be installed. This selection process of hydrants typically take days for a large site. An automatic selection process is needed to simplify the selection and installation processes, especially for large scale deployment of an acoustic propagation detection system. This automatic process requires an acoustical understanding of how far a leak noise can propagate to be able to place the computing node adequately. The present disclosure allows to save time, reduce the manual effort, and removes the subjective decision making of an operator in selecting a location for each computing node.

According to further aspects described herein, an automated selection process may be used that requires an acoustical understanding of how far a water leak noise can propagate to be able to place a computing node adequately combined with a geographic information system (GIS) in order to identify the possible locations for installation of computing nodes in a pipe network. According to further aspects described herein, the selection process may be reduced from days to minutes. According to further aspects described herein, for a given geographical area, the system may automatically identify if the distance between two water hydrants allows adequate acoustical propagation for leak detection. For example, if the distance will be acoustically covered, the system may display the corresponding pipe segment in Green, or depict the pipe segment as a solid line. If the distance may be covered, dependent on attenuation and pipe condition, the system may display the corresponding pipe segment in Yellow, or depict the pipe segment as a dashed line. If the distance is too long to ensure propagation for the given type of pipe, the segment may be displayed in Red, or depict the pipe segment as a dotted line. It will be appreciated by one skilled in the art that another visual indication to decipher the three different labeled lines on a map for the propagation distances may be used.

Figure 2:
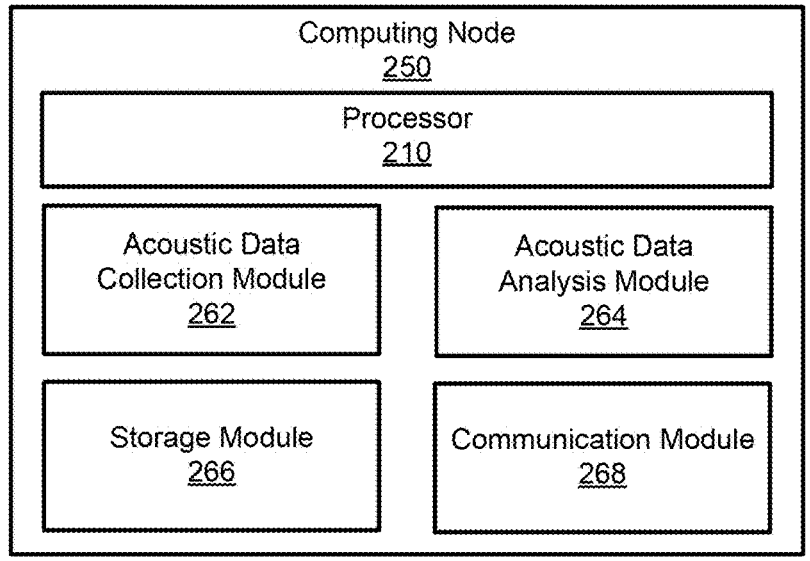
FIG. 2 illustrates a block diagram of a computing node to collect and analyze acoustic data for condition assessment and leak detection within a fluid distribution system according to examples of the present disclosure.
Figure 3:
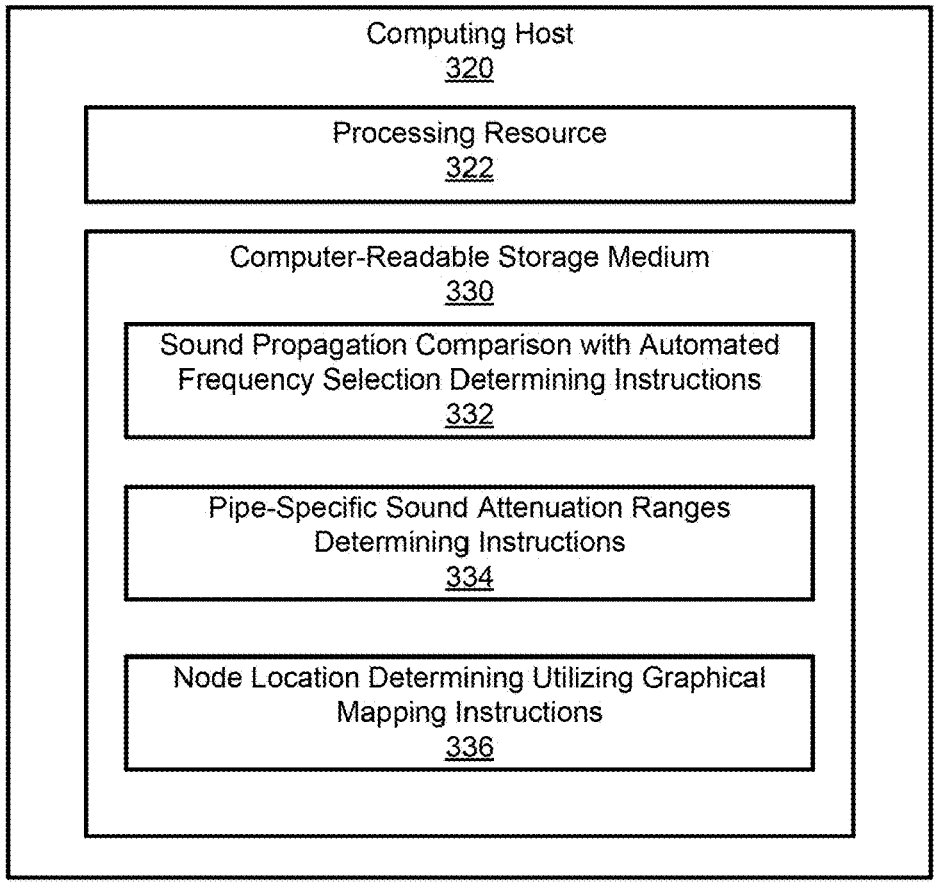
FIG. 3 illustrates a computing system including a computer-readable storage medium storing instructions to analyze the data collected within a fluid distribution system according to examples of the present disclosure.

FIGS. 1-3 illustrate particular components, modules, instructions, engines, etc. according to various examples as described herein. In different implementations, more, fewer, and/or other components, modules, instructions, engines, arrangements of components/modules/instructions/engines, etc. may be used according to the teachings described herein. In addition, various components, modules, engines, etc. described herein may be implemented as instructions stored on a computer-readable storage medium, as hardware modules, as special-purpose hardware (e.g., application specific hardware, application specific integrated circuits (ASICs), as embedded controllers, hardwired circuitry, etc.), or as some combination or combinations of these.

Generally, FIGS. 1-3 relate to components and modules of a computing system, such as computing host 120 of FIG. 1 and computing host 320 of FIG. 3 as well as components and modules of a computing node, such as computing nodes 150A-150N (also referred to herein generally as computing nodes 150) of FIG. 1 and computing node 250 of FIG. 2. It should be understood that the computing hosts and/or computing nodes may comprise any appropriate type of computing system and/or computing device, including for example smartphones, tablets, desktops, laptops, workstations, servers, smart monitors, smart televisions, digital signage, scientific instruments, retail point of sale devices, video walls, imaging devices, peripherals, networking equipment, wearable computing devices, metering devices, data collection devices, leak detecting devices, or the like.

FIG. 1 illustrates a diagram of an environment 100 to collect and analyze acoustic data within a fluid distribution system 110, according to examples of the present disclosure. As will be further described herein, computing nodes 150 of FIG. 1 collect and analyze acoustic data relating to the fluid distribution system 110. The acoustic data collected by the computing nodes 150 is transmitted to computing host 120 which performs analysis on the received data to determine condition assessment such as pipe degradation based on loss from the pipe wall thickness, predict pipe attenuation based on the type of pipe and soil type, and/or determine efficient and reliable location utilizing graphical mapping.

As illustrated, the environment 100 comprises the fluid distribution system 110, which may further comprise various components such as pipes, hydrants, valve, couplers, corporation stops, metering devices, etc. Although illustrated as a pipe, it should be understood that the fluid distribution system 110 may be a plurality of pipes and other fluid distribution system components connected together to form the fluid distribution system 110, of which the pipe is a portion.

Generally, the fluid distribution system 110 may be used to distribute fluids such as water to customers of a utility provider, for example. The fluid distribution system 110 may comprise various and numerous components, such as pipes, hydrants, valves, couplers, corporation stops, metering devices, and the like, as well as suitable combinations thereof. In examples, the fluid distribution system 110 may be partially or wholly subterranean, or portions of the fluid distribution system 110 may be subterranean, while other portions of the fluid distribution system 110 may be non-subterraneous (i.e., above ground). For example, a component of the fluid distribution system 110 may be partially or wholly subterraneous while another component (e.g., a hydrant, a valve, a testing device, etc.) connected to the first component and may be partially or wholly non-subterraneous. In other examples, the component may be partially subterranean in that the component has portions exposed, such as to connect certain devices (e.g., computing nodes 150, a hydrant, a valve, a testing device, etc.) to the fluid distribution system 110.

The computing nodes 150 monitor certain aspects of the fluid distribution system 110 and/or aspects of a fluid flowing through the fluid distribution system 110, illustrated as fluid path 112 within the fluid distribution system 110. In examples, the computing nodes 150 are in fluid communication with fluid path 112 within the fluid distribution system 110. In other examples, the computing nodes 150 are connected to a component of the fluid distribution system 110 and are not in fluid communication with the fluid path 112. As illustrated in FIG. 1, the computing nodes 150 are connected to a pipe of the fluid distribution system 110. In examples, the connection may be direct and/or indirect. More particularly, the computing nodes 150 may be connected directly to a pipe of the fluid distribution system 110, such as through a hole drilled into the wall of the pipe or via a coupling member (not shown) of the pipe, thereby causing the computing nodes 150 (or a sensor of the computing nodes 150) to be in fluid communication with the fluid path 112. In another example, computing nodes 150 may be connected indirectly to the pipe, such as via another component in the fluid distribution system 110 (e.g., a hydrant, a valve, a coupler, a corporation stop, metering device, etc.). Although four computing nodes 150A-N are illustrated, it should be understood that any suitable number of computing nodes are possible in various examples. In examples, the computing nodes 150 are placed in or connected to existing components of the fluid distribution system 110, such as a fire hydrant. A computing node 150 may be connected to each fire hydrant within a fluid distribution system, for example, or may be placed within a certain distance of another node (e.g., within 500 feet, within 1500 feet, etc.)

The computing nodes 150 collect and analyze acoustic data concerning the fluid distribution system 110. For example, the computing nodes 150 may collect a first acoustic data set synchronized with a known time reference for the purpose of detecting and locating a leak through correlation. The first acoustic data set may be compressed before transmission. The computing nodes 150 may then collect a second acoustic data set, which may include multiple acoustic data recordings to discriminate between persistent and transient processes. The second acoustic data set may then be analyzed by computing host 120 to determine if a leak is present, determine condition assessment such as pipe degradation percentage based on loss from the pipe wall thickness, predict pipe attenuation based on the type of pipe and soil type, and/or determine efficient and reliable location by implementing a graphical map.

As described below regarding FIG. 3, the computing nodes 150 may comprise various components, modules, engines, etc., such as an acoustic data collection module, an acoustic data analysis module, an acoustic data compression module, an acoustic data transmission module, a power supply, a data transmitter, a data receiver, an antenna, etc. The data transmitter, data receiver, and/or antenna may be used to wirelessly transmit and/or receive signals, commands, and/or data to and from other devices, including the computing host 120 such as via the network 140 and a communications hub 142 across communication links 144-148.

The dotted lines of FIG. 1 illustrate communicative links between and among the computing nodes 150, the communication hub 142, and the computing host 120, including a communication link 144 (between the communication hub 142 and the computing host 120), a communication link 146 (between the communication hub 142 and a network 140), and communication links 148 (between the network 140 and the computing nodes 150). These links generally represent a network or networks that may comprise hardware components and computers interconnected by communications channels that enable sharing of resources and information. The network 140 may comprise one or more of a cable, wireless, fiber optic, or remote connection via a telecommunication link, an infrared link, a radio frequency link, a cellular link, a Bluetooth® link, or any other suitable connectors or systems that provide electronic communication. The network 140 may comprise, at least in part, an intranet, the internet, or a combination of both. The network 140 may also comprise intermediate proxies, routers, switches, load balancers, and the like. The paths followed by the network between the devices as depicted in FIG. 1 represent the logical communication links between the computing nodes 150, the communication hub 142, the network 140, and the computing host 120, not necessarily the physical paths or links between and among the devices.

The communication hub 142 may include a precise time reference such as global positioning system ("GPS") coordinates, and distributes the time information throughout the network. In other aspects, each computing node 150 may include a time reference such as GPS coordinates. The computing nodes 150 collect and analyze acoustic data, as described herein. Each day, at specified times and periods, the computing nodes 150 may collect acoustic data and send information regarding the collected and analyzed data to the computing host 120.

The computing host 120 may comprise a processing resource 122 that represents generally any suitable type or form of processing unit or units capable of processing data or interpreting and executing instructions. The processing resource 122 may be one or more central processing units (CPUs), microprocessors, and/or other hardware devices suitable for retrieval and execution of instructions. The instructions may be stored, for example, on a memory resource (not shown), such as a computer-readable storage medium 330 of FIG. 3, which may comprise any electronic, magnetic, optical, or other physical storage device that store executable instructions. Thus, the memory resource may be, for example, random access memory (RAM), electrically-erasable programmable read-only memory (EPPROM), a storage drive, an optical disk, and any other suitable type of volatile or non-volatile memory that stores instructions to cause a programmable processor (e.g., the processing resource 122) to perform the techniques described herein. In examples, the memory resource comprises a main memory, such as a RAM in which the instructions may be stored during runtime, and a secondary memory, such as a non-volatile memory in which a copy of the instructions is stored.

Additionally, the computing host 120 may comprise an analysis engine 124 which is configured to analyze acoustic data received from the computing nodes 150. In examples, the engine(s) described herein may be a combination of hardware and programming. The programming may be processor executable instructions stored on a tangible memory, and the hardware may comprise processing resource 122 for executing those instructions. Thus a memory resource (not shown) can be said to store program instructions that when executed by the processing resource 122 implement the engines described herein. Other engines may also be utilized to include other features and functionality described in other examples herein.

Alternatively or additionally, the computing host 120 may comprise dedicated hardware, such as one or more integrated circuits, Application Specific Integrated Circuits (ASICs), Application Specific Special Processors (ASSPs), Field Programmable Gate Arrays (FPGAs), or any combination of the foregoing examples of dedicated hardware, for performing the techniques described herein. In some implementations, multiple processing resources (or processing resources utilizing multiple processing cores) may be used, as appropriate, along with multiple memory resources and/or types of memory resources.

The analysis engine 124 is configured to perform various analyses of the data received from the computing nodes 150. For example, each day, when the computing nodes 150 send information regarding the collected and analyzed data to the computing host 120, the computing host 120 analyzes the received data. Objectives of the analysis are to determine pipe degradation based on loss from the pipe wall thickness, predict pipe attenuation based on the type of pipe and soil type, and/or determine efficient and reliable location utilizing graphical mapping. The analysis engine 124 may determine adjacencies among the computing nodes 150 and perform correlation of the acoustic data for adjacent nodes (e.g., nodes within adjacencies). The correlation may include analyzing acoustic data received from adjacent nodes. According to some aspects, the correlation analysis may use any known method in the art. The computing host 120 may comprise additional engines, such as a data receiving engine to receive data from the computing nodes 150. The data may comprise raw acoustic data, and compressed acoustic data.

Although not shown in FIG. 1, it should be appreciated that the computing host 120 may comprise additional components. For example, the computing host 120 may comprise a display. The display may comprise a monitor, a touchscreen, a projection device, and/or a touch/sensory display device. The display may display data in the form of text, images, and other appropriate graphical content. The computing host 120 may further comprise a network interface to enable the computing host 120 to communicate via the communication link 148 with the computing nodes 150, with additional computing nodes, with other computing systems, and/or with other suitable devices. The computing host 120 may further implement a web server and a corresponding web application that allows multiple users to visualize the aforementioned data and configure the system remotely, over the network. The computing host 120 also implements a notification system that may notify users of a relevant event. The computing host 120 may also comprise any suitable input and/or output device, such as a mouse, keyboard, printer, external disk drive, touchscreen, microphone, or the like. The computing host 120 may also comprise an antenna (not shown) to wirelessly transmit and/or receive signals, commands, and/or data to and from other devices, including the computing nodes 150 such as via the communication hub 142 and the network 140 across the communication links 144-148.

FIG. 2 illustrates a block diagram of a computing node 250 to collect and analyze acoustic data within a fluid distribution system, such as fluid distribution system 110, according to examples of the present disclosure. The computing node 250 may represent any of computing nodes 150 of FIG. 1 and/or the computing nodes illustrated in FIGS. 4 and 16A-C. The computing node 250 monitors certain aspects of the fluid distribution system and/or aspects of a fluid flowing through the fluid distribution system. In examples, the computing node 250 is in fluid communication with the fluid path 112 within the fluid distribution system. In other examples, the computing node 250 is connected to a component of the fluid distribution system that is not in fluid communication with the fluid path 112.

In examples, the computing node 250 may comprise various components, modules, engines, etc., such as a processor 210, an acoustic data collection module 262, an acoustic data analysis module 264, a storage module 266, and a communications module 268. The processor 210 may comprise one or more of a microcontroller unit (MCU), a digital signal processor (DSP), and other processing elements.

The acoustic data collection module 262 may collect a first acoustic data at the computing node 250. The acoustic data collection module 262 also collects second acoustic data at the computing node 250. The acoustic data may be collected using a sensor or sensors of the computing node 250. Although not illustrated, the computing node 250 may comprise a piezoelectric sensor, hydrophone, or other similar sensor to detect an acoustic signal. The acoustic signal is then collected by the acoustic data collection module 262 as acoustic data (e.g., first acoustic data, second acoustic data, etc.). According to further aspects, the acoustic data analysis module 264 may analyze the acoustic data by comparing the collected second acoustic data to reference acoustic data, as well as perform other data analysis on the acoustic data as described herein.

The storage module 266 may include flash memory, read-only memory (ROM), random access memory (RAM), or other types of memory. The storage module 266 may comprise a database for storing acoustic data collected by the acoustic data collection module 262. The database may include frequency bins for storing current acoustic data as well as historic data collected over several days. According to some aspects, the processor 210 may be configured to utilize the stored acoustic data to detect the presence or probability of leaks, bursts, or tampering activity.

The communication module 268 may transmit the acoustic data to the computing host (e.g., computing host 120 of FIG. 1 and/or computing host 320 of FIG. 3). The communication module 268, which may comprise a data receiver, a data transmitter, a data transceiver, and/or an antenna may be used to wirelessly transmit and/or receive signals, commands, and/or data to and from other devices, including the computing host via a network and/or a communications hub across a communication link or links.

In examples, the computing node 250 may comprise other components which, although not illustrated, may comprise a power supply, a data receiver, an antenna, an input device, additional sensors, etc.

FIG. 3 illustrates a computing system including a computer-readable storage medium 330 storing instructions 332-336 to analyze data collected within a fluid distribution system according to examples of the present disclosure. The computer-readable storage medium 330 is non-transitory in the sense that it does not encompass a transitory signal but instead is made up of one or more memory components configured to store the instructions 332-336. The computer-readable storage medium 330 may be representative of a memory resource and may store machine executable instructions 332-336, which are executable on a computing system such as computing host 120 of FIG. 1 as well as the computing host 320 of FIG. 3 in conjunction with processing resource 322.

In the example shown in FIG. 3, the instructions 332-336 comprise sound propagation comparison with automated frequency selection determining instructions 332, pipe-specific sound attenuation ranges determining instructions 334, and node location determining utilizing graphical mapping instructions 336. The instructions 332-336 of the computer-readable storage medium 330 may be executable so as to perform the techniques described herein, including the functionality described regarding the method 500 of FIG. 5, the method 900 of FIG. 9, and the method 1500 of FIG. 15.

Figure 5:
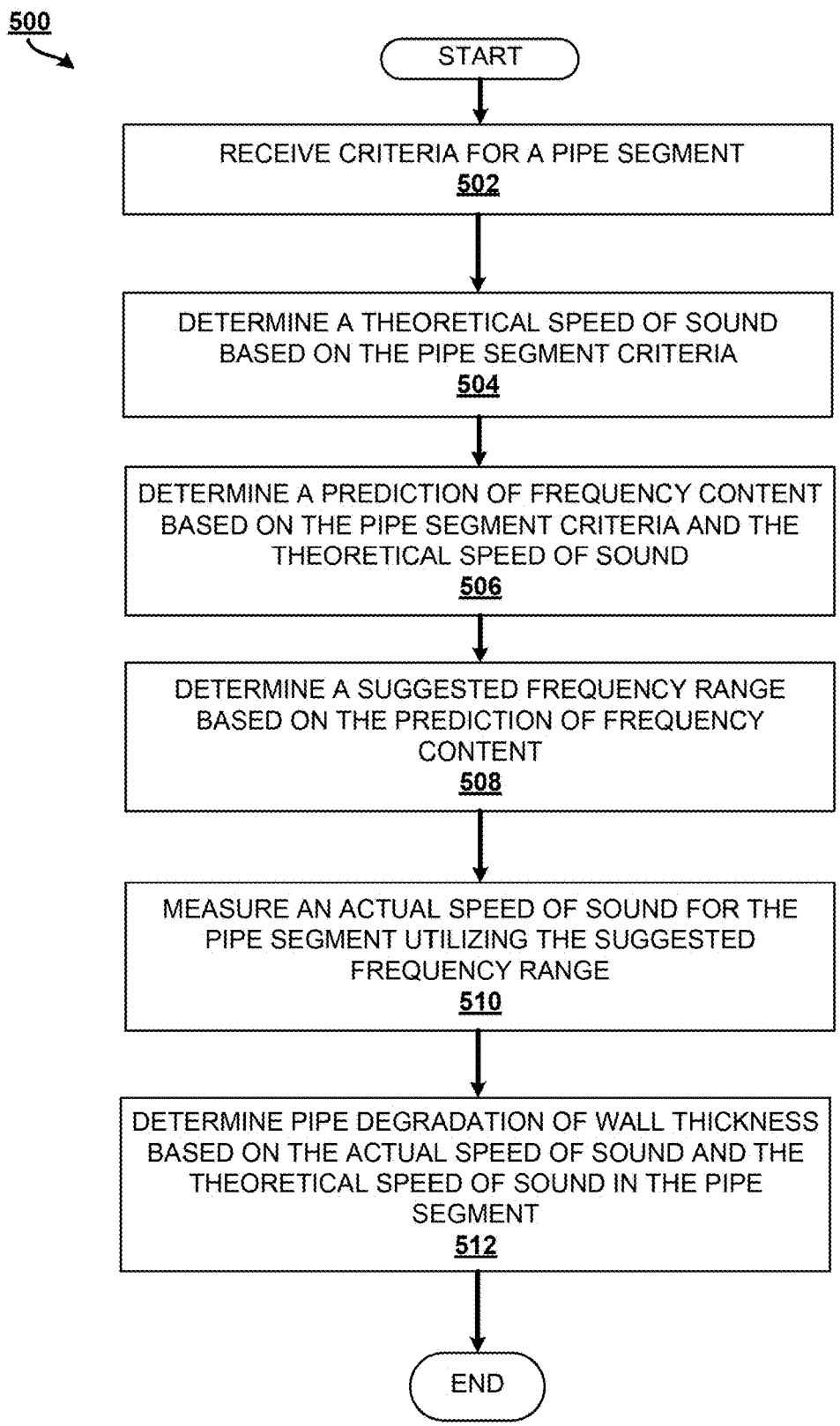
FIG. 5 illustrates a flow diagram of a method to analyze data collected within a fluid distribution system and determine pipe degradation utilizing predicted frequency content according to examples of the present disclosure.

For example, the sound propagation comparison with automated frequency selection determining instructions 332 may correspond to blocks 502-512 of FIG. 5. The pipe-specific sound attenuation ranges determining instructions 334 may correspond to blocks 902-908 of FIG. 9. Finally, the node location determining utilizing graphical mapping instructions 336 may correspond to blocks 1502-1508 of FIG. 15. The functionality of these instructions 332-336 is described below with reference to the functional blocks of FIGS. 5, 9, and 15, respectively, but should not be construed as so limiting.

Figure 4:
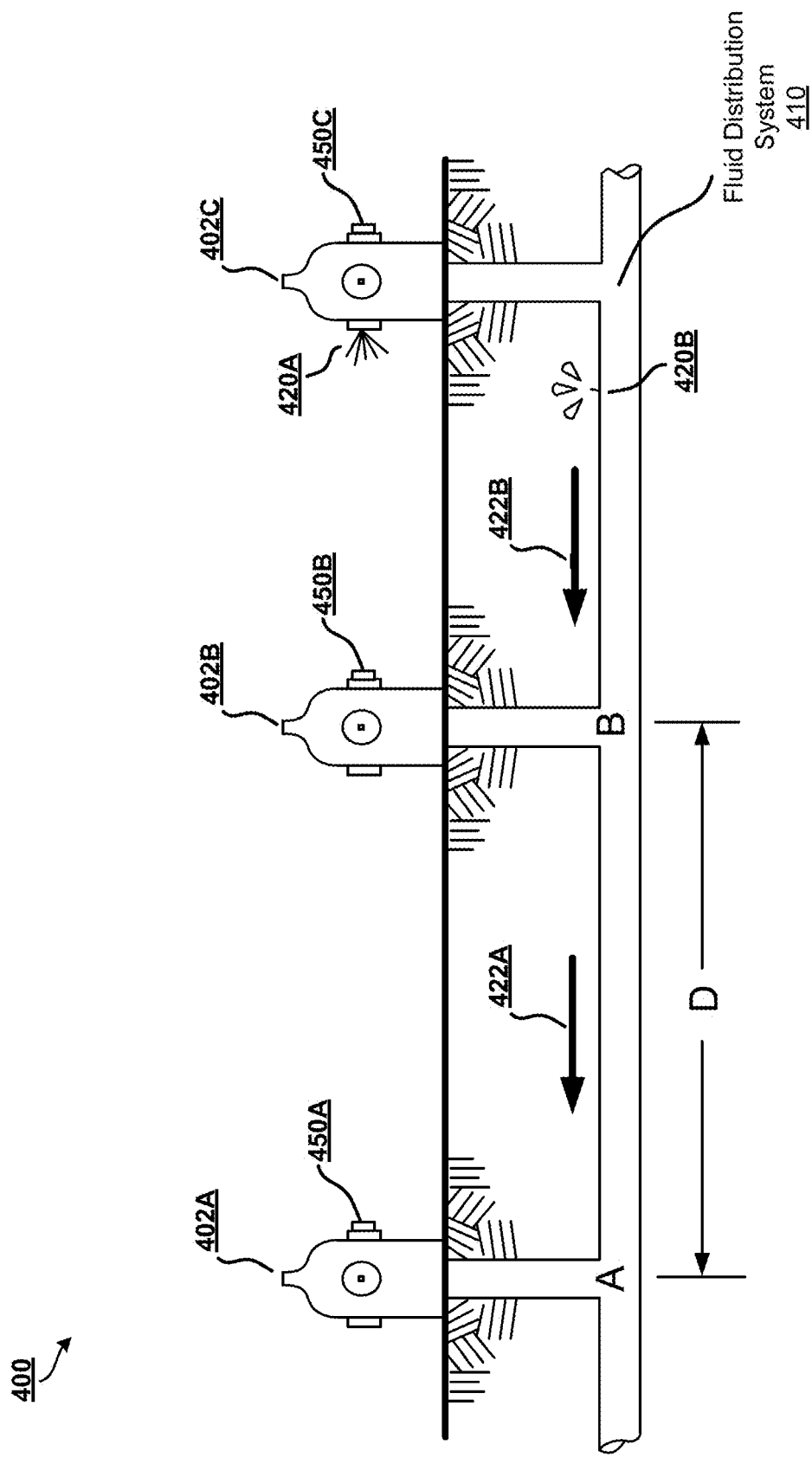
FIG. 4 illustrates a diagram of a fluid distribution system with a noise source and computing nodes attached to components of the fluid distribution system for collecting and analyzing acoustic data for condition assessment and leak detection according to examples of the present disclosure.

FIG. 4 illustrates diagram 400 of a fluid distribution system 410 with computing nodes 450A-450O (also referred to herein generally as computing nodes 450) for collecting and analyzing acoustic data within the fluid distribution system according to examples of the present disclosure. The fluid distribution system 410 may comprise pipes and other components (e.g., valves, couplings, fittings, meters, hydrants, etc.) used to carry fluids (e.g., water, gas, etc.) such as to customer locations. According to various aspects of the present disclosure, computing nodes 450 may be attached to the fire hydrants 402A-402O (also referred to herein generally as fire hydrants 402). In some aspects, computing nodes 450 may be attached to each hydrant 402 while other aspects may include attachment with about every other one of the hydrants 402. In FIG. 4, for example, three adjacent fire hydrants 402A-C are shown, connected to a pipe of the fluid distribution system 410 for detecting a noise, such as noise source 420A or leak 420B. Because of the nature of a water leak, such as leak 420B, acoustic signals or vibration signals can be detected on the components (e.g., pipes, fire hydrants 402, etc.) of the fluid distribution system 410. Particularly, computing nodes 450 may be mounted on the pipes themselves or may be mounted on the hydrants 402. Optionally, when two leak detectors, adjacent on the fluid distribution system 410 such as computing nodes 450 mounted on hydrants 402 nearest to the leak 420B, are able to pick up acoustic signals with sufficient strength, the signals may be used to detect the presence and location of a leak. Alternatively, a computing node 450 may be located in a meter, in another communication device, as a stand-alone unit, or in any other piece of utility equipment that interfaces with the fluid distribution system 410.

According to some aspects, an intentional noise may be implemented, such as noise source 420A, in order to gather acoustic data between two computing nodes 450. For example, a user may be acquiring data in order to analyze a segment of a pipe for condition assessment. The pipe segment, for example, may be between points A and B on FIG. 4. The user may be collecting and analyzing data from computing node 450A on hydrant 402A and computing node 450B on hydrant 402B, and generating noise source 420A by hitting hydrant 402C with a hammer, for example. The sound velocity 422A-B from noise source 420A is then propagated through the pipe and the computing nodes 450 than collect the acoustic data created by the noise source 420A. This data is then analyzed and a speed of sound in the water-filled pipe is computed, as further discussed herein.

FIG. 5 illustrates a flow diagram of a method 500 to analyze data collected within a fluid distribution system and determine pipe degradation utilizing predicted frequency content according to examples of the present disclosure. The method 500 may be executed by a computing system or a computing device such as computing host 120 of FIG. 1. The method 500 may also be stored as instructions on a non-transitory computer-readable storage medium such as computer-readable storage medium 330 of FIG. 3 that, when executed by a processing resource (e.g., processing resource 122 of FIG. 1 and/or processing resource 322 of FIG. 3), cause the processing resource to perform the method 500.

At block 502, the method 500 begins and comprises receiving criteria for a pipe segment in order to determine condition assessment by calculating pipe degradation for the pipe segment. An exemplary pipe segment may be illustrated in FIG. 4 as the pipe segment between points A and B. According to some aspects, the criteria may be manually entered by a technician or another user of the system. According to other aspects, these values may be automatically populated by the computing host as known information for a pipe segment as stored in a table. According to other aspects, these values may be automatically calculated. The pipe segment criteria may include pipe characteristics, water characteristics, and a length of the pipe segment (e.g., a distance D between computing nodes 450A and 450B, as shown in FIG. 4). The pipe characteristics may comprise a young modulus, an inner diameter, a wall thickness, and a lining thickness. The water characteristics may comprise a bulk modulus, a temperature, a background pressure, and a background velocity.

Next, at block 504, the method 500 comprises determining a theoretical speed of sound based on the pipe segment criteria that was received at block 502 utilizing equations known in the art for calculating propagation velocity of acoustic waves in a pipe. For example, propagation velocity of acoustic waves in an unbounded fluid body may be defined by the following equation:

$$v_0 = \sqrt{\frac{K}{\rho}}$$

where K is the bulk modulus of elasticity of the fluid and $\rho$ is its density. According to some aspects, a velocity of acoustic waves for thin-walled pipe with a uniform cross-section may be calculated, and is defined by the following equation:

$$v = \frac{v_0}{\sqrt{1 + c\frac{DK}{tE}}}$$

where D is the diameter of the pipe, t is the wall thickness, E is the elastic modulus of the pipe material, and c is a factor that takes into account the fixation method of the pipe. According to some aspects, the velocity of acoustic waves for a thick-walled pipe with expansion joints throughout its length may be calculated, and is defined by the following equation:

$$v = \frac{v_0}{\sqrt{1 + \frac{DK}{tE}\left(\frac{2t}{D}(1+\mu) + \frac{D}{D+t}\right)}}$$

where $\mu$ is the Poisson's ratio of the pipe material. According to some aspects, the velocity of acoustic waves for a thick-walled pipe with constrained axial movement may be calculated, and is defined by the following equation:

$$v = \frac{v_0}{\sqrt{1 + \frac{DK}{tE}\left(\frac{2t}{D}(1+\mu) + \frac{D}{D+t}(1-\mu^2)\right)}}$$

Next, at block 506, the method 500 comprises determining a prediction of frequency content based on the pipe segment criteria from block 502, and the calculated theoretical speed of sound from block 504. Examples of prediction of frequency content are illustrated in FIGS. 6A-6D.

Figure 6A:
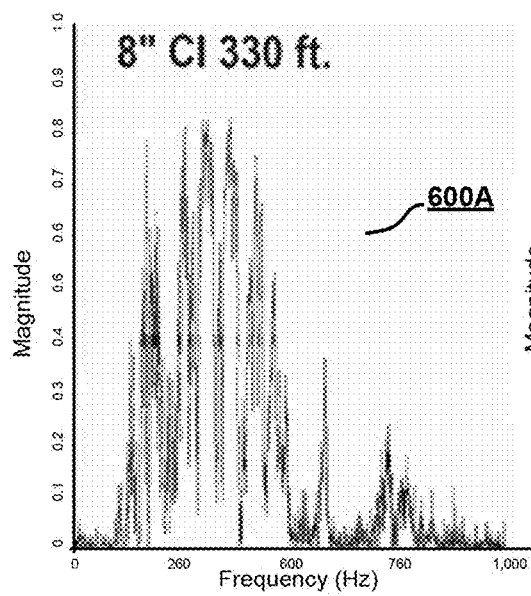
FIGS. 6A-6B illustrate graphs of data of measured frequency content data relating to the techniques for collecting and analyzing data and creating prediction models within a fluid distribution system according to examples of the present disclosure.
Figure 6B:
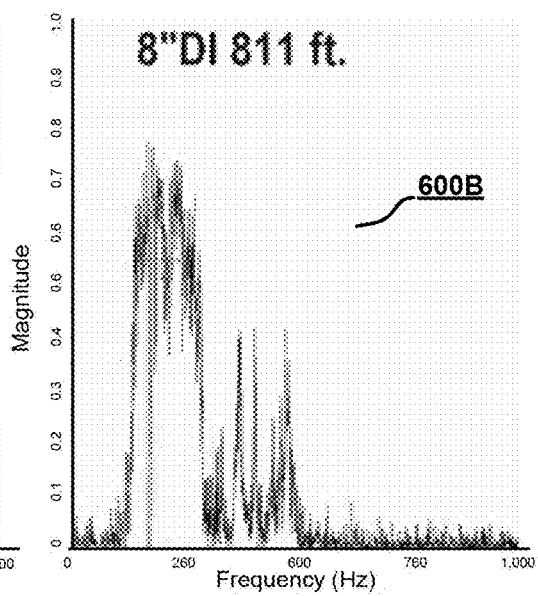

FIGS. 6A-6D illustrate graphs 600A-600D of data relating to the techniques for collecting and analyzing data and creating prediction models within a fluid distribution system according to examples of the present disclosure. In particular, FIGS. 6A and 6B illustrate graphs 600A and 600B, respectively, of measured frequency content data within a fluid distribution system according to examples of the present disclosure. For example, graph 600A illustrates measured frequency content of a cast iron ("CI") pipe, with a diameter of 8 inches and a length of 330 feet. Graph 600B illustrates measured frequency content of a ductile iron ("DI") pipe, with a diameter of 8 inches and a length of 811 feet.

Figure 6C:
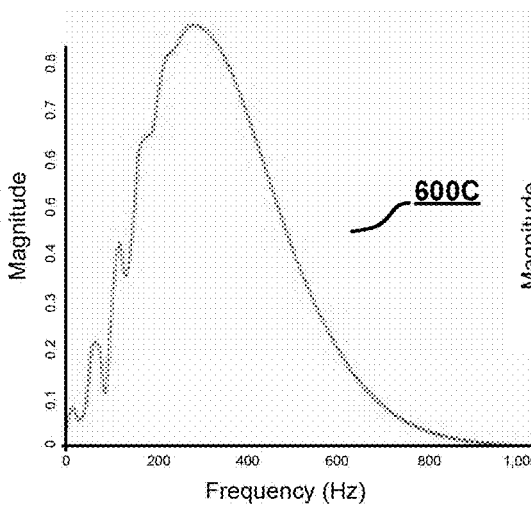
FIGS. 6C-6D illustrate graphs of data of predicted frequency content data relating to the techniques for collecting and analyzing data and creating prediction models within a fluid distribution system according to examples of the present disclosure.
Figure 6D:
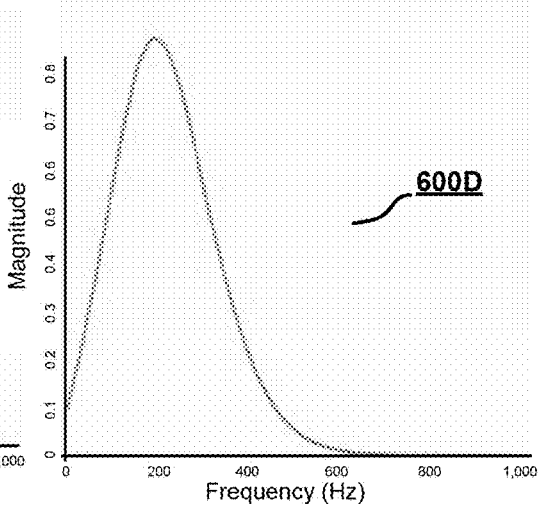

FIGS. 6C and 6D illustrate graphs 600C and 600D, respectively, of predicted frequency content data relating to the techniques for collecting and analyzing data within a fluid distribution system according to examples of the present disclosure. In particular, FIGS. 6C and 6D illustrate a cross-spectrum density (CSD) function characterizing the acceleration of the wall that has the shape of a band-pass filter. According to some aspects, the band-pass filter may be a combination of a fixed high-pass cut-off and a variable low-pass cut-off for different distances.

According to some aspects, the pipe system may act as a low-pass filter as higher frequencies attenuate quicker, where the acoustic pressure wave may propagate along the pipe system and may be attenuated as it travels away from the source. The attenuation, as described further herein, may depend on factors such as the distance, the frequency, the losses in the wall (or damping) and the soil attenuation. Thus, the cut-off frequency of this low-pass filter, may depend on distance from the source, properties of the wall material, and soil composition. According to some aspects, the pressure wave in the water medium transfers to the wall, where the wall acts as a spring-mass system which behaves as a high-pass filter. Thus, the cut-off frequency depends on the elastic properties of the wall material.

According to an exemplary aspect, graph 600C illustrates predicted frequency content of the same pipe illustrated in FIG. 6A, a CI pipe, with a diameter of 8 inches and a length of 330 feet. Graph 600D illustrates predicted frequency content of the same pipe illustrated in FIG. 6B, a DI pipe, with a diameter of 8 inches and a length of 811 feet.

Referring back to FIG. 5, after a prediction for frequency content is determined at block 506, next, at block 508, the method 500 comprises determining a suggested frequency range for an acoustic propagation detection system, or the like, to utilize to measure actual speed of sound based on the prediction of frequency content. An example of determining a suggested frequency range is illustrated in FIG. 7.

Figure 7:
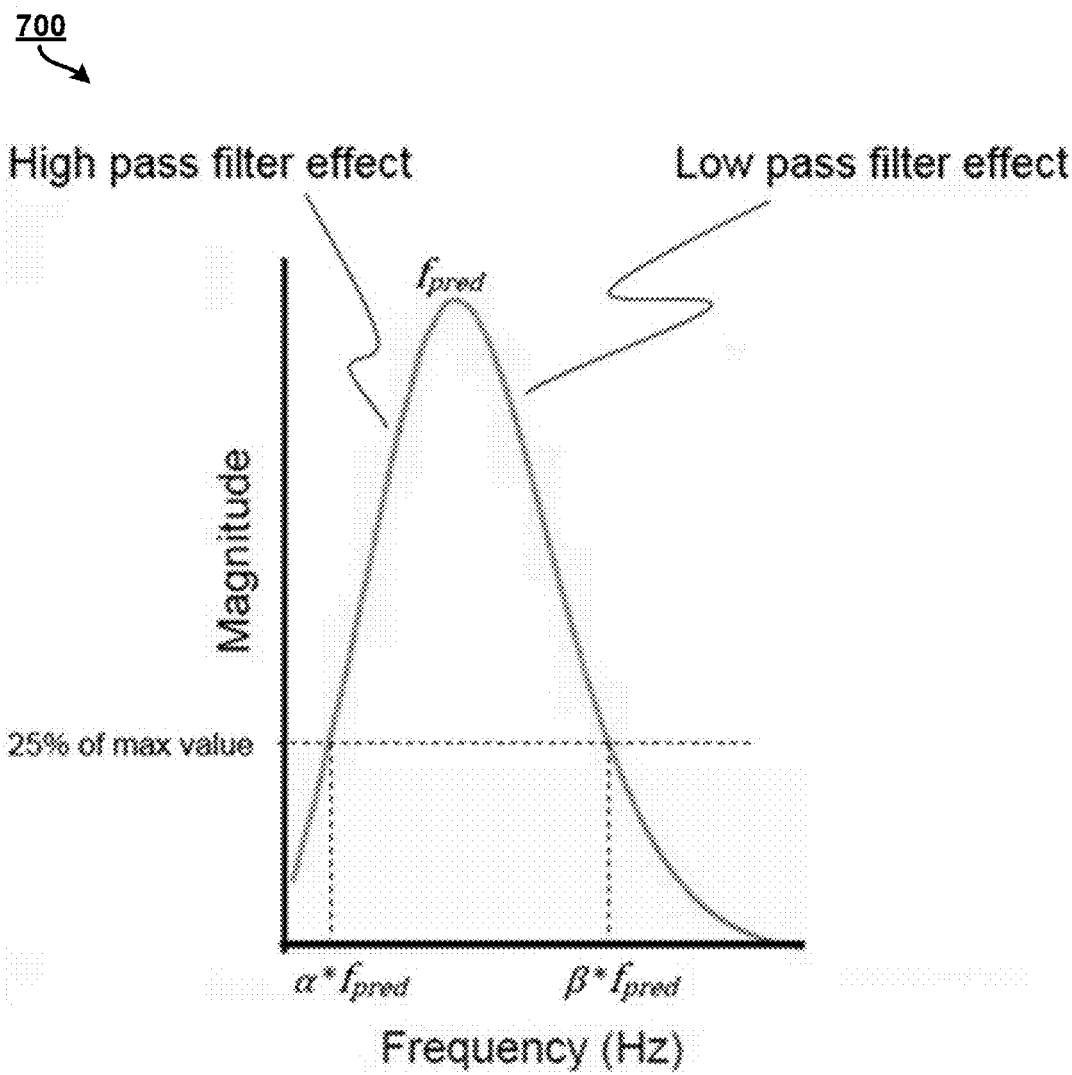
FIG. 7 illustrates a graph of data relating to the techniques for collecting and analyzing data and creating prediction models within a fluid distribution system according to examples of the present disclosure.

FIG. 7 illustrates graph 700 of data relating to the techniques for collecting and analyzing data and creating prediction models within a fluid distribution system according to examples of the present disclosure. In particular, FIG. 7 illustrates graph 700 of hypothetical frequency content data in order to illustrate how a suggested frequency range may be calculated. For example, first an explicit frequency is predicted for a specific type of pipe using the following analytical equation:

$$f_{pred} = \sqrt{\frac{v^2}{\pi dD}}$$

where v is the speed of sound in the pipe (velocity of acoustic waves), d is the distance between the acoustical sensors, and D is the diameter of the pipe. Following the calculation for an explicit frequency, a suggested frequency range may be calculated. and is defined by the following equation:

$$[\alpha * f_{pred}, \beta * f_{pred}]$$

where $\alpha$ and $\beta$ are two empirical parameters that may be identified using a statistical analysis on the attenuation of pipes.

Referring back to FIG. 5, after a suggested frequency range is determined at block 508, next, at block 510, the method 500 comprises measuring an actual speed of sound with an acoustic propagation detection system for the pipe segment utilizing the suggest frequency range calculated at block 508. According to some aspects, the acoustic propagation detection system may be an Echologics EchoShore-DX system, or other known systems in the art for measuring speed of sound in a pipe segment between two nodes of a utility system. According to some aspects, a speed of sound in a water-filled pipe from measurement ($v_m$) may be calculated, and is defined by the following equation:

$$v_m = \frac{d}{\Delta t}$$

where d is the distance between two acoustical sensors, such as computing nodes 450A and 450B, and $\Delta t$ is the time delay between the signals detected by the same two acoustical sensors, such as sound velocity 422A acquired by computing node 450A, and sound velocity 422B acquired by computing node 450B, as illustrated in FIG. 4. According to some aspects, Δt may be obtained using a correlation function known in the art.

Finally, at block 512, the method 500 comprises determining pipe degradation based on loss of the pipe wall thickness of the pipe segment based on the actual speed of sound as measured at block 510, and the theoretical speed of sound calculated at block 504. According to some aspects, the pipe degradation based on loss from the pipe wall thickness may be calculated by using the appropriate equation for the velocity of acoustic waves in pipes as described herein. In that case, the remaining wall thickness $t_{rem}$ is a function depending on the parameters D, K, E, c, μ, $v_m$ and $v_0$. The pipe degradation, in percent, ($DEG_\%$) is calculated by comparing the current wall thickness (remaining thickness) to the original wall thickness (nominal thickness, $t_{nom}$) with the following equation:

$$DEG_\% = 100 * \left( \frac{t_{rem} - t_{nom}}{t_{nom}} \right)$$

Figure 8:
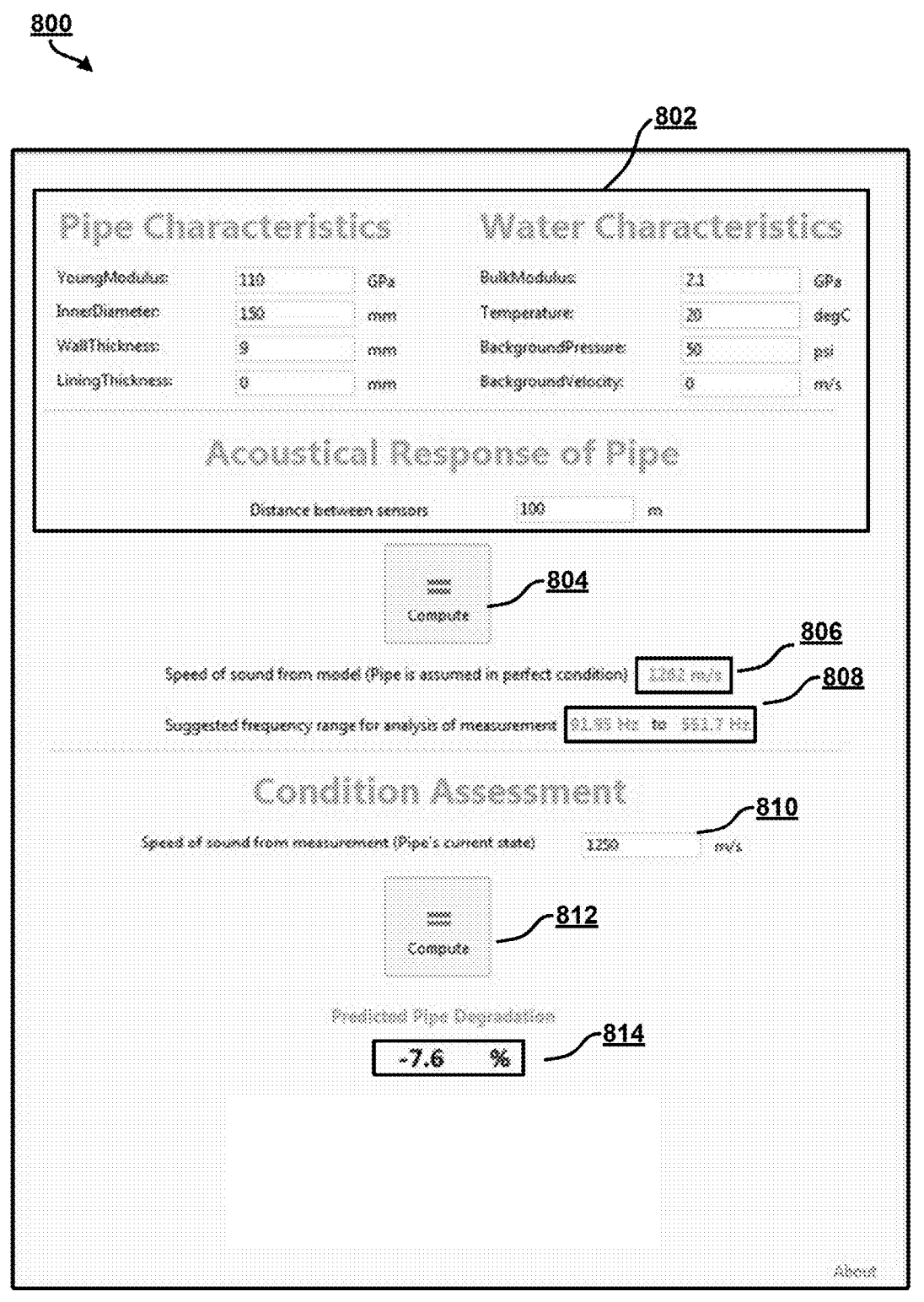

FIG. 8 illustrates a screen diagram of a user interface to analyze data collected within a fluid distribution system according to examples of the present disclosure. In particular, FIG. 8 illustrates an example screenshot 800 relating to the method 500 described above in regard to FIG. 5 for implementing a method to determine pipe degradation utilizing predicted frequency content. In this example aspect, as discussed herein for block 502 of method 500, a user can manually enter in the pipe segment criteria as pipe characteristics, water characteristics, and a length of the pipe segment ("Distance between sensors") in the fields of block 802. Once the pipe segment criteria has been entered, a user may select the first compute option 804, and the system will calculate and display a theoretical speed of sound (block 806), determine a prediction of frequency content, and calculate and display a suggested frequency range (block 808) as discussed herein for blocks 504-508 of method 500. According to the example aspect, a user may then enter the suggested frequency range from block 808 into their acoustic propagation detection system, and enter the measured speed of sound into field 810 as discussed herein for block 510 of method 500. Once the pipe segment criteria has been entered, and an actual speed of sound has been entered, a user may select the second compute option 812, and the system will calculate and display a predicted pipe degradation (block 814) as discussed herein for block 512 of method 500.

According to some aspects, the acoustic propagation detection system used to measure the speed of sound may communicate with the pipe degradation calculation system, and may automatically measure the speed of sound after the suggest frequency range has been calculated and display the measurement on field 810. According to some aspects, the acoustic propagation detection system and the pipe degradation calculation system may be the same system, and thus may also automatically measure the speed of sound after the suggested frequency range has been calculated and display the measurement on field 810.

Figure 9:
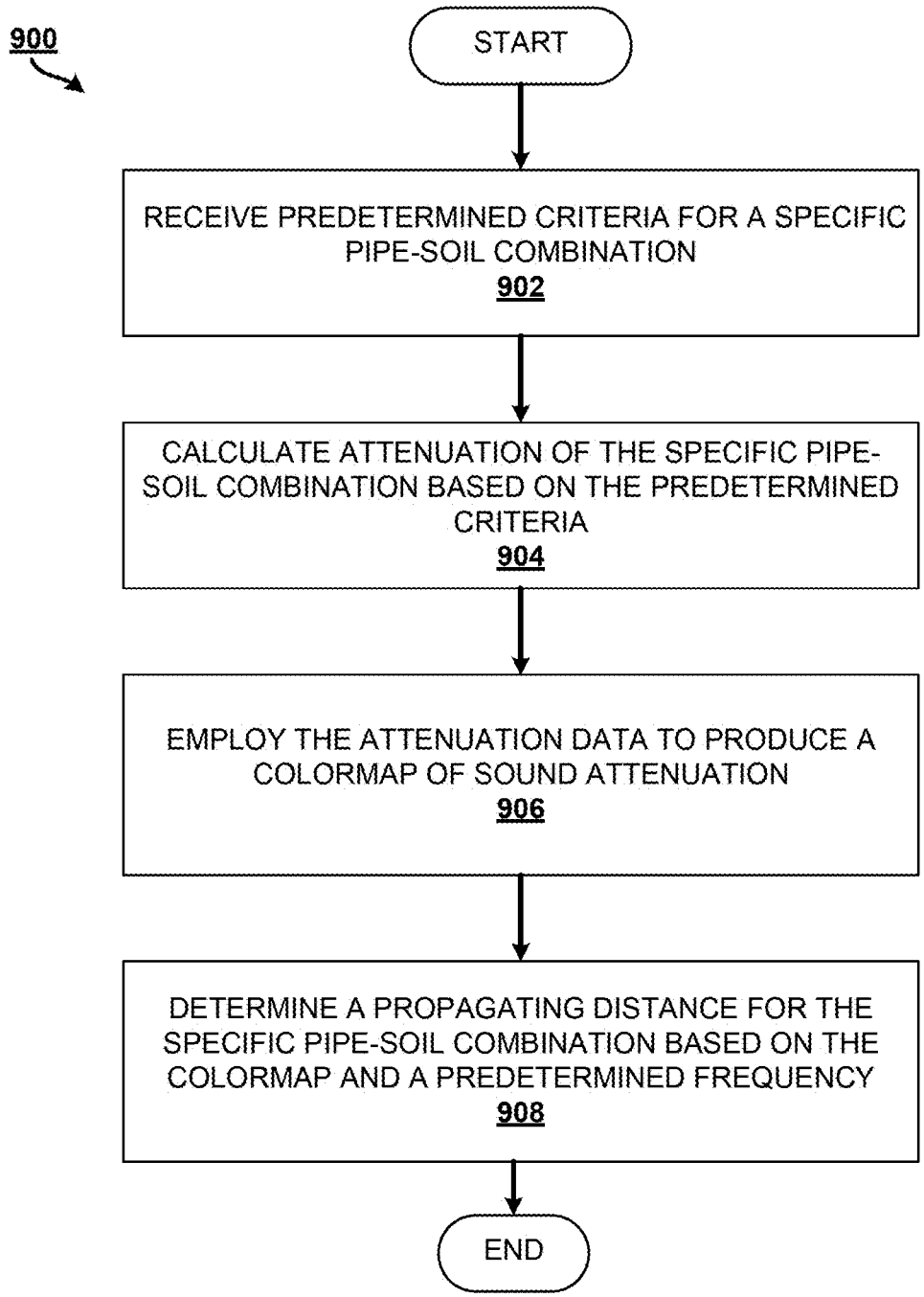
FIG. 9 illustrates a flow diagram of a method to collect and analyze data to generate and utilize pipe-specific sound attenuation ranges within a fluid distribution system according to examples of the present disclosure.

FIG. 9 illustrates a flow diagram of a method 900 to collect and analyze data to generate and utilize pipe-specific sound attenuation ranges within a fluid distribution system according to examples of the present disclosure. The method 900 may be executed by a computing system or a computing device such as computing host 120 of FIG. 1. The method 900 may also be stored as instructions on a non-transitory computer-readable storage medium such as computer-readable storage medium 330 of FIG. 3 that, when executed by a processing resource (e.g., processing resource 122 of FIG. 1 and/or processing resource 322 of FIG. 3), cause the processing resource to perform the method 900.

At block 902, the method 900 begins and comprises receiving predetermined criteria for a specific pipe-soil combination. According to some aspects, the predetermined criteria may be manually entered by a technician or another user of the system. According to other aspects, these values may be automatically populated by the computing host as known information for a pipe segment as stored in a table. The predetermined criteria may comprise damping within the pipe wall (η), the diameter of the pipe (D), the Bulk modulus of water (K), the elastic modulus of the pipe material (E), the wall thickness (t), and the free-field water wavespeed ($c_0$). According to some aspects, the free-field water wavespeed $c_0$ may comprise the propagation velocity of acoustic waves in an unbounded fluid body.

Next, at block 904, the method 900 comprises determining an attenuation based on the pipe-soil criteria that was received at block 902. For example, predicting pipe attenuation based on the type of pipe and soil type may be determined by calculating a specific combination pipe—soil attenuation coefficient ($\lambda_{tot}$). For an above ground pipe, the attenuation coefficient λ is related to the loss in the pipe-wall and may be defined by the following equation:

$$\lambda = \frac{1}{v_0} \frac{\eta DK/2Et}{\sqrt{\left(1 + \frac{DK}{Et}\right)}}$$

According to aspects described herein, the surrounding medium, e.g. the soil, may be considered as a virtual layer on the outside of the pipe wall. Thus, the attenuation from the soil may be applied directly with the loss in the pipe-wall to predict the overall attenuation of a specific combination pipe-soil. The specific combination pipe-soil attenuation coefficient ($\lambda_{tot}$) may be defined by the following equation:

$$\lambda_{tot} = \frac{1}{v_0} \frac{(\eta + \eta_{soil})DK/2Et}{\sqrt{\left(1 + \frac{DK}{Et}\right)}}$$

where $\eta_{soil}$ is the damping from the surrounding medium, e.g., the soil. The different types of soil may be classified by soil code and soil series. An example soil classification table for six types of commonly found soil, is illustrated in Table 1 below.

TABLE 1

| Classification of soils | | |
|---|---|---|
| Soil Code | Soil series | Soil classification |
| ADA | Adrian | sandy or sandy-skeletal mixed, euic, mesic Terric Haplosaprists |
| CAB | Catlin | fine-silty, mixed, superactive mesic, Oxyaquic Argindolls |
| DRA | Drummer | fine-silty, mixed, superactive, mesic, Typic Endoaquolls |
| MEA | Medway | fine-loamy, mixed, superactive, |

TABLE 1-continued

Classification of soils

| Soil Code | Soil series | Soil classification |
|---|---|---|
| PLA | Plainfield | mesic, Fluvaquentic Hapludolls mixed, mesic Typic Udipsamment |
| SAC | Sable | fine-silty, mixed, superactive mesic, Typic Endoaquolls |

Each type of soil may have a unique combination of four components: clay, silt, sand, and organic matter. Based on a review known in the art of several soil types listed in Table 1, the range of variation for the attenuation coefficient of soils was determined to be predominantly in the following range: $0.3 < \eta_{soil} < 1$. According to some aspects, if the specific soil classification where its pipe network is buried is known, a specific attenuation coefficient for that specific soil type may be determined.

According to some aspects, for a specific combination pipe-soil, the attenuation (A) is a function of the specific combination pipe-soil attenuation coefficient ($\lambda_{tot}$), a frequency, and a distance from the source, and may be defined by the following equation:

$$A = e^{-\lambda_{tot} \omega d}$$

where $\omega$, the angular frequency, and $d$, the distance from the source, are two variables. According to some aspects, utilizing this equation a colored graphical illustration (or "colormap" as described herein) may be obtained where w varies along the x-axis and d varies along the y-axis. For any combination of these two variables, the equation may provide a value of attenuation which may be colored to provide the colormap. The attenuation in dB ($A_{dB}$) may be defined by the following equation:

$$A_{dB} = 20 \log_{10}(A)$$

Next, at block 906, the method 900 comprises employing the attenuation data from block 904 to produce a colormap of sound attenuation. Examples of colormaps and an illustration for propagating distances for different types of pipes are illustrated in FIGS. 10-14.

FIGS. 10-14 illustrate graphs 1000, 1100A,B, 1200A,B, 1300A,B, and 1400 of data relating to the techniques for collecting and analyzing data to generate and utilize pipe-specific sound attenuation ranges within a fluid distribution system according to examples of the present disclosure. In particular, graphs 1000, 1100A,B, 1200A,B, 1300A,B, and 1400 may represent data analyzed using the method 900, for example.

Figure 10:
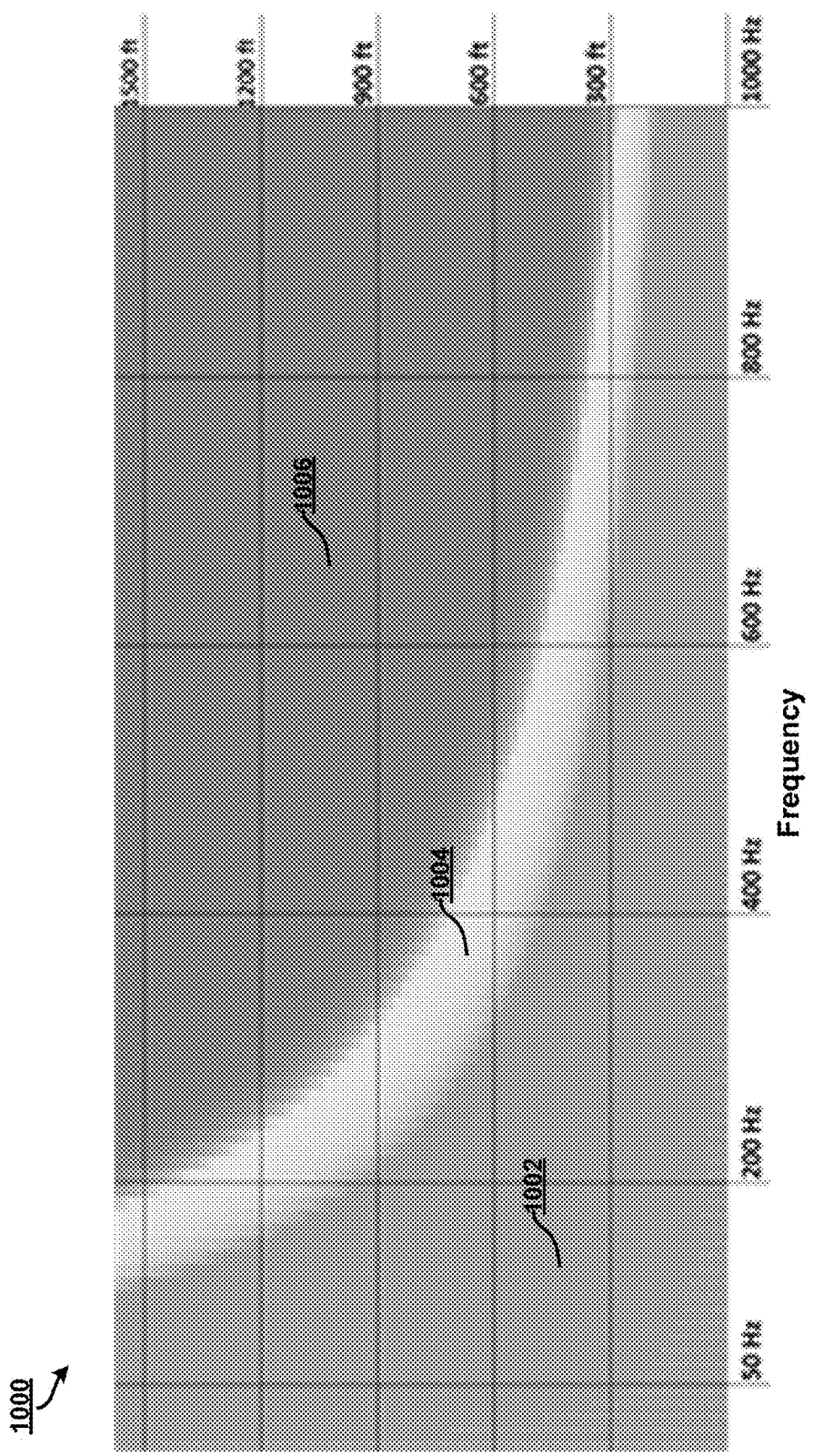
FIG. 10 illustrates an example colormap relating to the techniques for collecting and analyzing data to generate and utilize pipe-specific sound attenuation ranges within a fluid distribution system according to examples of the present disclosure.

FIG. 10 illustrates graph 1000 as an example colormap with utilization of the formulation in dB to visualize attenuation data. For the colormaps described herein, the "Green" area 1002 represents an attenuation below 40 dB, the "Yellow" area 1004 represents an attenuation between 40 and 60 dB, and the "Red" area 1006 represents an attenuation above 60 dB. According to aspects described herein, by using the colormap visualization, it is possible to identify equivalent propagating distances for specific types of pipes and different soil types. It will be appreciated by one skilled in the art that the colomaps described herein, e.g. FIGS. 10-14 are shown as black and white in the drawings, but represent actual colors on a computer screen or display. For example, "Green" area 1002 would be green, "Yellow" area 1004 would be yellow, and "Red" area 1006 would be red on an exemplary computer display.

FIGS. 11-13 illustrate colormap graphs for a specific type and diameter of pipe using high attenuation from soil (e.g., 0.3) to identify the shortest propagating distance, and using low attenuation from soil (e.g., 0.1) to identify the longest propagating distance. For example, FIG. 11A illustrates graph 1100A as a colormap for a cast iron pipe, six inches in diameter, with high attenuation from the soil to identify the shortest distance of propagation. Therefore, at 90 Hz (the specific frequency for metallic pipes used by the acoustic propagation detection system, EchoShore-DX, as described herein), the shortest distance for propagation (located at approximately 50 dB in the "Yellow" area 1004) is approximately 580 feet. Similarly, FIG. 11B illustrates colormap 1100B for the same cast iron pipe, six inches in diameter, but now the longest distance of propagation is identified using low attenuation from the soil. Therefore, at 90 Hz, the longest distance for propagation (located at approximately 40 dB in the "Yellow" area 1004) for a cast iron pipe, 6 inches in diameter, is approximately 1000 feet.

FIG. 12A illustrates graph 1200A as a colormap for a steel pipe, ten inches in diameter, with high attenuation from the soil to identify the shortest distance of propagation. Therefore, at 90 Hz (the specific frequency for metallic pipes used by the acoustic propagation detection system, EchoShore-DX, as described herein), the shortest distance for propagation (located at approximately 50 dB in the "Yellow" area 1004) is approximately 750 feet. Similarly, FIG. 12B illustrates colormap 1200B for the same steel pipe, ten inches in diameter, but now the longest distance of propagation is identified using low attenuation from the soil. Therefore, at 90 Hz, the longest distance for propagation (located at approximately 40 dB in the "Yellow" area 1004) for a cast iron pipe, 6 inches in diameter, is approximately 1300 feet.

FIG. 13A illustrates graph 1300A as a colormap for a plastic pipe, eight inches in diameter, with high attenuation from the soil to identify the shortest distance of propagation. Therefore, at 10 Hz (the specific frequency for plastic pipes used by the acoustic propagation detection system, Echo-Shore-DX, as described herein) the shortest distance for propagation (located at approximately 50 dB in the "Yellow" area 1004) is approximately 340 feet. Similarly, FIG. 13B illustrates a colormap 1300B for the same plastic pipe, eight inches in diameter, but now the longest distance of propagation is identified using low attenuation from the soil. Therefore, at 10 Hz the longest distance for propagation (located at approximately 40 dB in the "Yellow" area 1004) for a plastic pipe, 8 inches in diameter, is approximately 585 feet.

Referring back to FIG. 9, after the colormap for the specific pipe is produced at block 906, next, at block 908, the method 900 comprises determining a propagating distance for the specific pipe-soil combination based on the colormap and a predetermined frequency, as illustrated by FIGS. 11-13.

Figure 14:
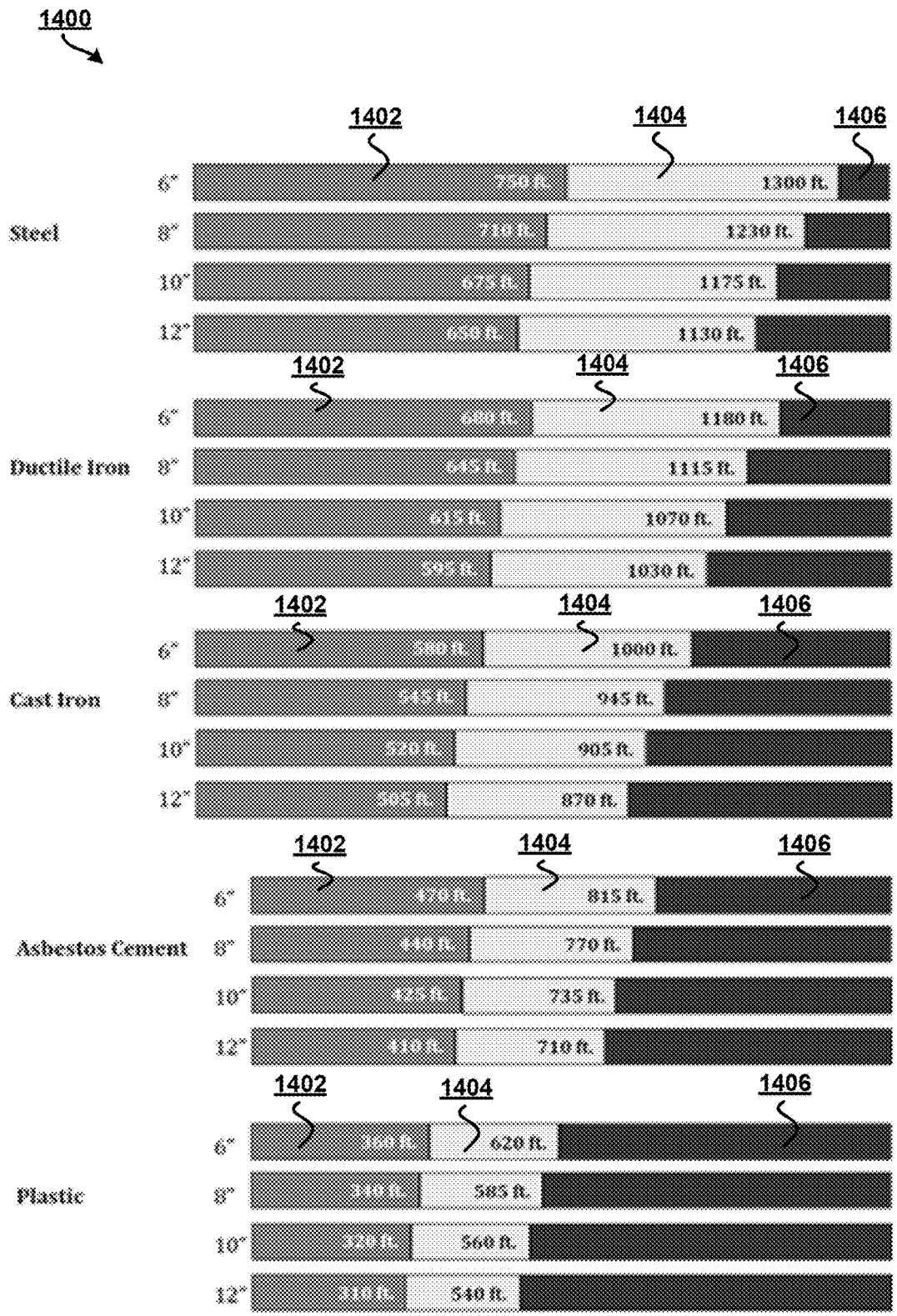
FIG. 14 illustrates a graph of example propagating distances for different types of pipes relating to the techniques for collecting and analyzing data to generate and utilize pipe-specific sound attenuation ranges within a fluid distribution system according to examples of the present disclosure.

FIG. 14 illustrates a graph 1400 of example propagating distances for different types of pipes based on attenuation as calculated using the method 900, for example. For each type of pipe, the parameters of a specific pipe are entered into a computing system or a computing device such as computing host 120 of FIG. 1. Then, the longest distance a sound can propagate may be calculated using the soil with the least attenuation ($\eta_{soil}=0.3$), and the shortest distance of propagation may be calculated using the soil with the highest attenuation ($\eta_{soil}=1$), and is defined by the following equation:

$$d_{propagation} = \frac{A_{dB} * \ln(10)}{20 * \lambda_{tot} \times \omega_p}$$

where $\omega_p$ is a predetermined frequency, either selected by the user during a manual process or fixed by the settings of a leak detection system.

According to some aspects, the shortest distance may be calculated by the intersection between a specific frequency and the middle of the "Yellow" area 1404 which corresponds to an attenuation of ~50 dB. The longest distance may be calculated by using the intersection between a specific frequency and the bottom of the "Yellow" area 1404 which corresponds to an attenuation of ~40 dB. According to some aspects 60 dB may be used to calculate the shortest distance, however 50 dB is used in the exemplary aspect because it is based on the physical limitations of the leak detection system and its electronics related to the ability to distinguish a sound source from a background noise. Thus, if the sound source is attenuated with more than 50 dB, a typical system may not be able to discriminate between the two. Current state of the art produces acoustic sensors and electronics with a dynamic range of 40 dB to 60 dB, therefore, 50 dB is used as an exemplary aspect. For example, if the attenuation is below 40 dB, it may be expected that the sound source is always detectable because the sound level from the source is still strong enough. However, if the attenuation is above 60 dB, it may be expected that the sound source is not detectable anymore because the sound level is below detectable level, therefore, the 40 dB to 60 dB area is the uncertainty zone, e.g. "Yellow" area 1404.

According to an exemplary aspect as illustrated in FIG. 14, the "Green" area(s) 1402 for each example pipe tested (e.g. steel, ductile iron, cast iron, asbestos cement, and plastic) corresponds to an attenuation of below 40 dB, the "Yellow" area(s) 1404 represents an attenuation between 40 and 60 dB, and the "Red" area(s) 1406 represents an attenuation above 60 dB. It will be appreciated by one skilled in the art that the graph 1400, described herein for FIG. 14, is shown as black and white in the drawing, but represents actual colors on a computer screen or display. For example, "Green" area(s) 1402 would be green, "Yellow" area(s) 1404 would be yellow, and "Red" area(s) 1406 would be red on an exemplary computer display.

According to the exemplary aspect, for metallic pipes, the specific frequency used may be 90 Hz, and for plastic pipes, the specific frequency used may be 10 Hz. Each specific frequency in this exemplary aspect is corresponding to the settings of the EchoShore-DX system. However, the distances that are obtained using this approach are dependent on the frequency used, and these frequencies depend on the characteristics of the acoustic technology used to listen to the pipes. Therefore, according to other aspects, another acoustic propagation detection system known in the art may be used that utilize different frequencies for metallic and/or plastic pipes, thus the frequency to be used should be adapted based on the specific characteristics of the acoustic propagation detection system used.

According to the exemplary aspect, the associated values used to create FIG. 14 are dependent on the settings of the acoustical monitoring system and its sensitivity to sound. Therefore, it will be appreciated by one skilled in the art that it is expected that the values of distance for acoustical coverage will increase as a result of improvements made on the acoustical monitoring system, improving its sensitivity to sound.

Figure 15:
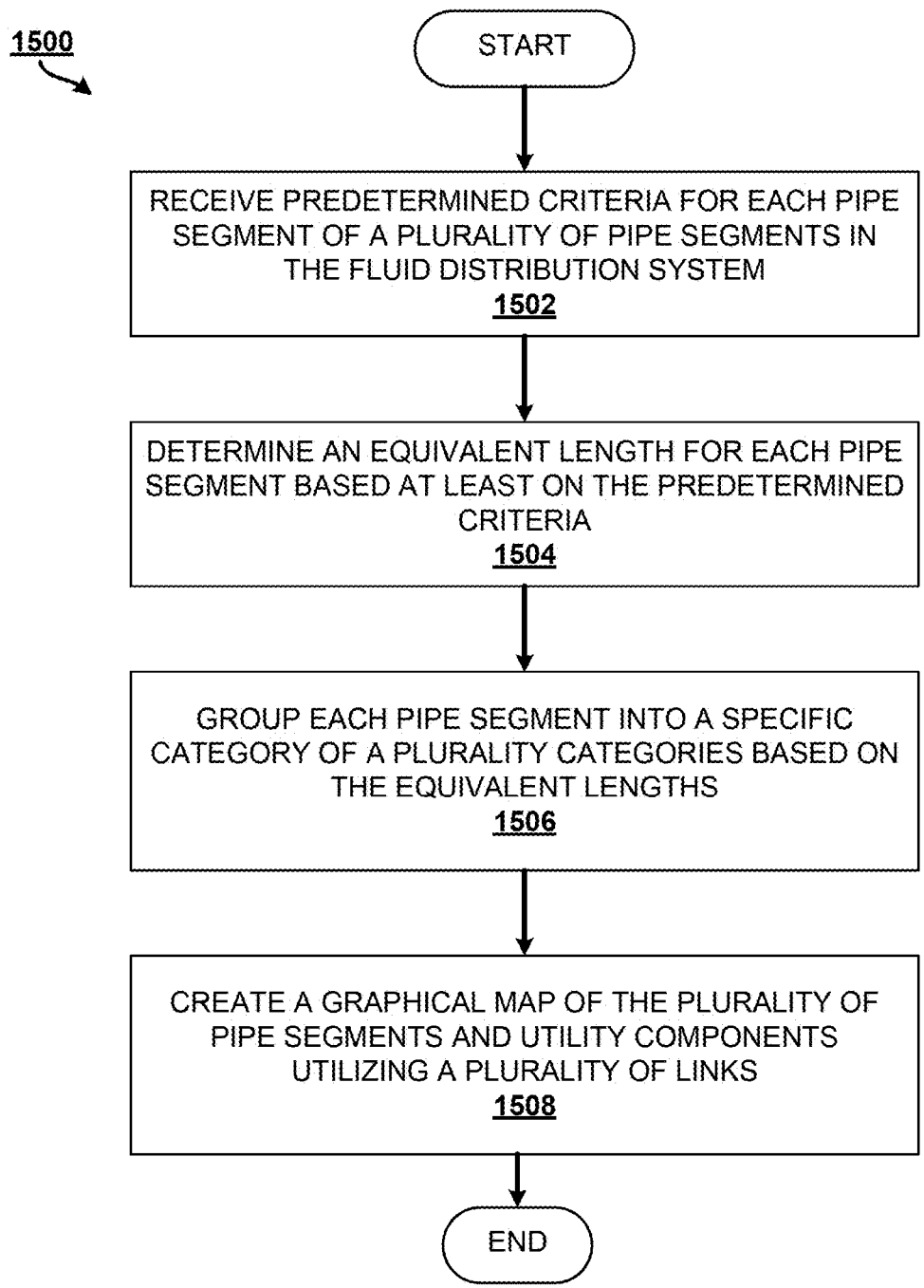
FIG. 15 illustrates a flow diagram of a method to analyze data collected within a fluid distribution system and determine computing node location selection utilizing graphical mapping according to examples of the present disclosure.

FIG. 15 illustrates a flow diagram of a method 1500 to analyze data collected within a fluid distribution system and determine computing node location selection utilizing graphical mapping according to examples of the present disclosure. The method 1500 may be executed by a computing system or a computing device such as computing host 120 of FIG. 1. The method 1500 may also be stored as instructions on a non-transitory computer-readable storage medium such as computer-readable storage medium 330 of FIG. 3 that, when executed by a processing resource (e.g., processing resource 122 of FIG. 1 and/or processing resource 322 of FIG. 3), cause the processing resource to perform the method 1500.

At block 1502, the method 1500 begins and comprises receiving predetermined criteria for each pipe segment of a plurality of pipe segments in a fluid distribution system for a given geographical area. According to some aspects, the predetermined criteria may be manually entered by a technician or another user of the system. According to other aspects, these values may be automatically populated by the computing host as known information for a pipe segment as stored in a table. The predetermined criteria may comprise a pipe material, a pipe diameter, and a length of a pipe segment.

Next, at block 1504, the method 1500 comprises determining an equivalent length for each pipe segment based on the pipe segment criteria that was received at block 1502. For example, to obtain a graphical map, geographical distance between two possible locations for installation of computing nodes is needed. According to aspects described herein, the distance between two possible locations for installation of computing nodes is defined as segment length. Depending on the type of pipe and pipe diameter, a coefficient (y) is applied to the segment length to calculate an equivalent length, and may be defined by the following equation:

Equivalent_Length=γ*Segment_Length where γ is a coefficient dependent on the type of pipe and pipe material. An example table of a list of coefficients for different types of pipes and materials is illustrated in Table 2 below.

TABLE 2

Coefficient for different types of pipes and materials

| | Steel | Ductile Iron | Cast Iron | Asbestos Cement | Plastic |
|---|---|---|---|---|---|
| 6 in | 1.000 | 1.100 | 1.300 | 1.600 | 2.100 |
| 8 in | 1.059 | 1.165 | 1.377 | 1.695 | 2.224 |
| 10 in | 1.108 | 1.218 | 1.440 | 1.772 | 2.326 |
| 12 in | 1.149 | 1.264 | 1.493 | 1.838 | 2.412 |

According to aspects described herein, a 6-inch diameter steel pipe may be used as a reference pipe, thus the coefficient y is 1.

Next, at block 1506, the method 1500 comprises grouping each pipe segment into a specific category of a plurality of categories based on the equivalent lengths. According to some aspects, the plurality of categories may comprise the following: Green, Yellow, and Red. The shortest distance and longest distances of propagation for equivalent length may be calculated, and then the system may group each pipe segment into one of three separate equivalent length categories: Green, Yellow, and Red. For example, the Green category may represent a calculated equivalent length of less than or equal to 750 feet, the Yellow category may represent a calculated equivalent length of greater than 750 feet and less than or equal to 1300 feet, and the Red category may represent a calculated equivalent length of greater than 1300 feet. According to aspects described herein, the Green category may represent pipe segments (lengths of pipe between two computing nodes) that the system determines that each computing node would be very likely to determine if a leak is present based on the propagation between the two computing nodes. According to aspects described herein, the Yellow category may represent pipe segments the system determines that each computing node would be somewhat likely be able to determine if a leak is present based on the propagation distance between the two computing nodes. According to aspects described herein, the Red category may represent pipe segments that the system determines that each computing node would not be very likely to determine if a leak is present based on the propagation distance (the equivalent length calculated) between two computing nodes.

According to aspects described herein, travelling distances for each type of pipe and pipe material, e.g. FIGS. 11-13, can be reversely determined by dividing 750 feet (shortest distance of propagation for the reference pipe—6-inch diameter steel pipe with a coefficient of 1.000) by the corresponding coefficient from Table 2 to obtain the shortest distance of propagation, and dividing 1300 feet (longest distance of propagation for the reference pipe—6-inch diameter steel pipe with a coefficient of 1.000) by the corresponding coefficient from Table 2 to obtain the longest distance of propagation. For example, FIGS. 11A-B illustrate colormaps of attenuation for a 6-inch diameter cast iron pipe, and a 6-inch diameter cast iron pipe has a coefficient y of 1.3 (Table 2); therefore, the shortest distance of propagation would be 750 feet divided by 1.3 (y), which equals ~577 feet, and the longest distance of propagation would be 1300 feet divided by 1.3 (y), which equals 1,000 feet.

Finally, at block 1508, the method 1500 comprises creating a graphical map of the plurality of pipe segments and utility components utilizing a plurality of links. According to some aspects, the plurality of links may comprise distinct visual indications based on the propagation category for each pipe segment. In addition, each utility component may comprise a corresponding computing node, such as such as computing nodes 450A and 450B. Examples of graphical mapping for propagating distances for a network of pipes in a given geographical area utilizing a plurality of links are illustrated in FIGS. 16A-16C.

Figure 16A:
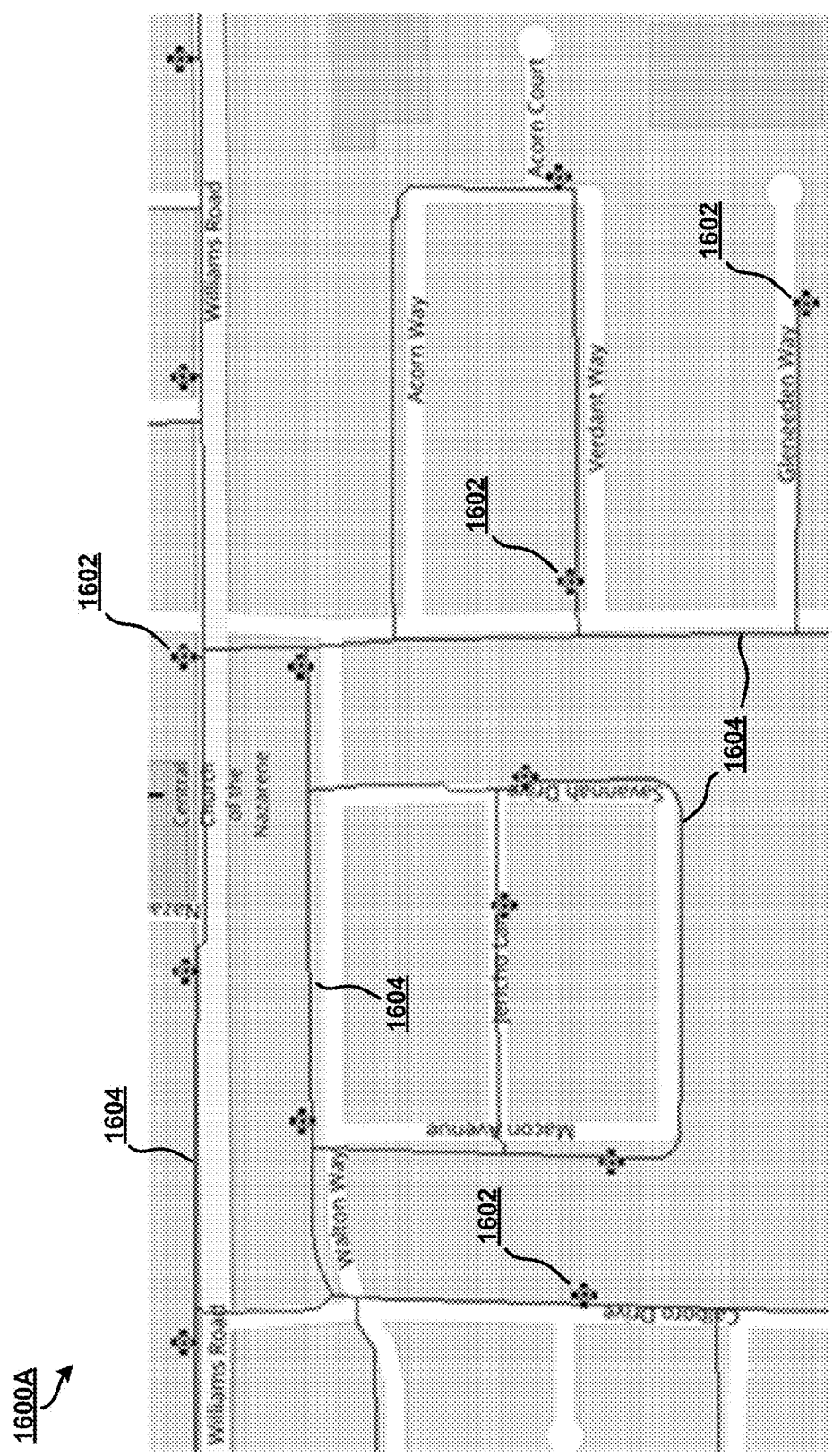
Figure 16B:
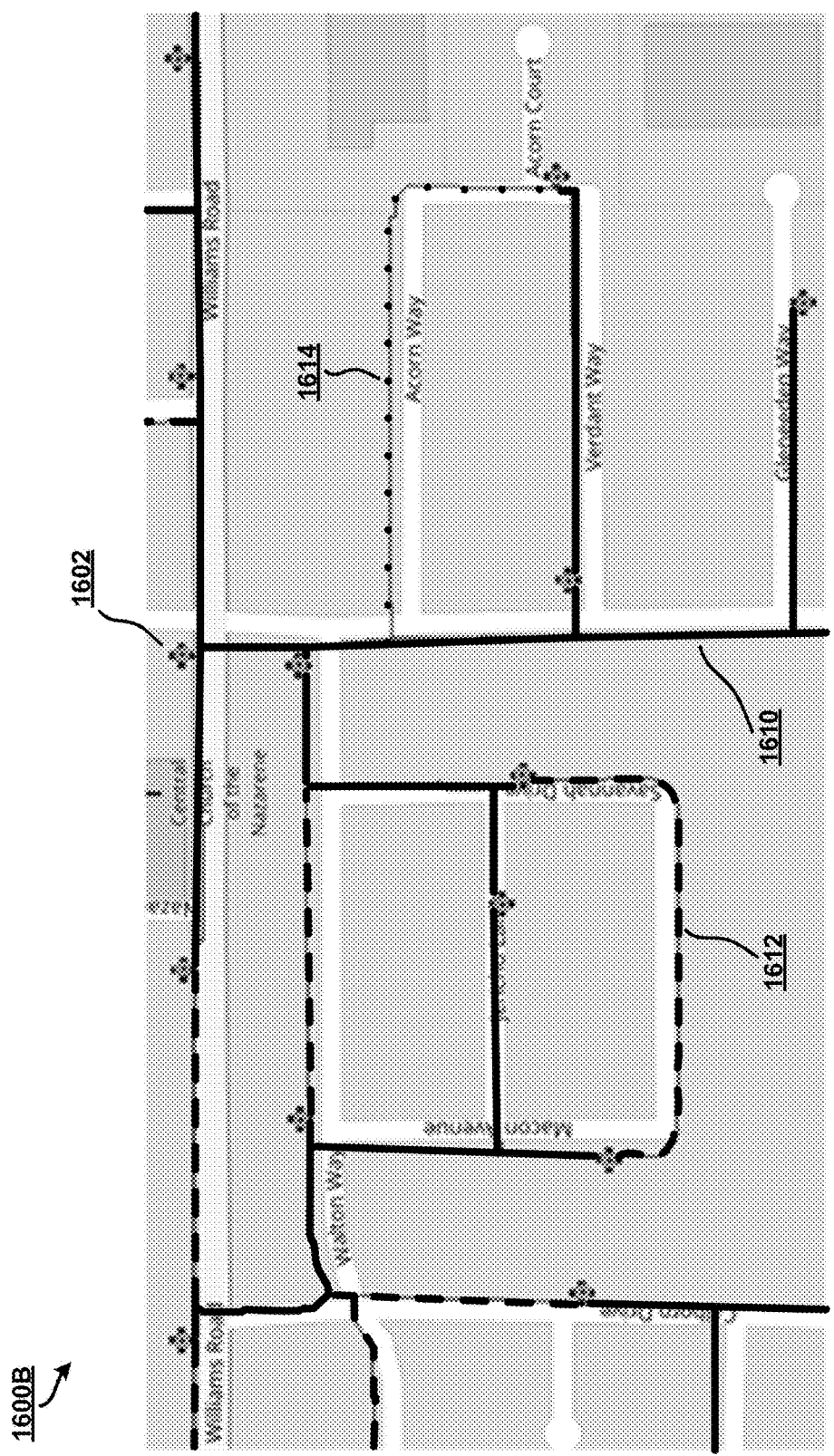

FIGS. 16A-16C illustrate diagrams 1600A-1600C of a fluid distribution system 1604 with computing nodes 1602 for collecting and analyzing acoustic data for graphical mapping of computing node location selection within the fluid distribution system according to examples of the present disclosure. The fluid distribution system 1604 comprises pipes and other components (e.g., valves, couplings, fittings, meters, hydrants, etc.) used to carry fluids (e.g., water, gas, etc.) such as to customer locations. The fluid distribution system 1604 may comprise computing nodes 1602 located at each hydrant, such as computing nodes 150 of FIG. 1, computing node 250 of FIG. 2, and/or computing nodes 450 of FIG. 4. In particular, the graphical map in diagram 1600A of FIG. 16A represents a given geographical area of a fluid distribution system 1604 with computing nodes 1602 installed at each hydrant.

According to some aspects, the physical pipe network information illustrated in FIG. 16A may be generated using geographic information system (GIS) data sourced from the customer's documentation whereas the graphical mapping of computing node location selection may be determined through a two-step process, and is shown in FIG. 16B. First, the system may automatically determine equivalent length propagation based on pipe segment criteria and divide those into three different propagation categories (Green, Yellow, and Red), as described by method 1500. Second, the system may generate a plurality of links that correlate to the three categories and may be overlaid on a pipe network map. For example, as illustrated in FIG. 16B (with a background street map) and FIG. 16C (without a background street map), three different types of plurality of links are shown: a solid line 1610 which may represent the Green category; a dashed line 1612 which may represent the Yellow category; and a dotted line 1614 which may represent the Red category. It will be appreciated by one skilled in the art that the plurality of links shown in diagrams 1600B,C, described herein for FIG. 16B,C, are shown as black and white lines (e.g. solid, dashed, and dotted) in the drawing, but represent actual colors on a computer screen or display. For example, a solid line 1610 may be shown as a solid green line, a dashed line 1612 may be shown as a solid yellow line, and a dotted line 1614 may be shown as a solid red line on an exemplary computer display.

According to some aspects, efficient computing node placement may be automatically determined and mapped out in order to determine which computing nodes may not be necessary to be installed on each hydrant and still be able to meet requirements for propagation and proper acoustic coverage (e.g., the Green and Yellow categories). According to some aspects, the system may determine where to place additional computing nodes for adequate acoustical propagation for leak detection if it is determined the equivalent length is too long to ensure propagation to detect a leak (e.g., the Red category). According to some aspects, the system may determine a specific computing node is not required for a specific utility component in order to ensure proper propagation measurement for leak detection. According to further aspects, the plurality of links on the graphical map may be automatically updated without the specific utility component for visual display to the user. Alternatively, the system may highlight the specific node that may be removed, allowing the user to determine if the system should remove the specific node, and if the user chooses to proceed, than the system would automatically update the graphical map and plurality of links accordingly.

According to some aspects, a user may use the system to toggle between the three different views of FIGS. 16A-C in order to acquire a better visualization the plurality of links with the map of the specific geographic region being analyzed for computing node selection location. According to some aspects, a user may select a particular computing node 1602 to be removed, and the system may automatically update the plurality of links such that the user can visualize the updated map with the specific computing node 1602 removed in order to determine if efficient propagation remains.

It should also be understood that conditional language, such as, among others, "can," "could," "might," or "may," unless specifically stated otherwise, or otherwise understood within the context as used, is generally intended to convey that certain examples comprise, while other examples do not comprise, certain features, elements and/or steps. Thus, such conditional language is not generally intended to imply that features, elements, and/or steps are in any way required for one or more particular examples or that one or more particular examples necessarily comprise logic for deciding, with or without user input or prompting, whether these features, elements and/or steps are included or are to be performed in any particular example.

It should be emphasized that the above-described examples are merely possible examples of implementations and set forth for a clear understanding of the present disclosure. Many variations and modifications may be made to the above-described examples without departing substantially from the spirit and principles of the present disclosure. Further, the scope of the present disclosure is intended to cover any and all appropriate combinations and sub-combinations of all elements, features, and aspects discussed above. All such appropriate modifications and variations are intended to be included within the scope of the present disclosure, and all possible claims to individual aspects or combinations of elements or steps are intended to be supported by the present disclosure.

What is claimed is:

1. A method for receiving and analyzing data for condition assessment within a fluid distribution system, comprising:
   receiving pipe segment criteria for a pipe segment, the pipe segment comprising a length of a pipe between a first computing node and a second computing node;
   determining a predicted parameter based on the received pipe segment criteria for the pipe segment;
   utilizing the predicted parameter to measure an actual speed of sound for the pipe segment between the first computing node and the second computing node; and
   comparing the actual speed of sound and a theoretical speed of sound to calculate a predicted pipe degradation for the pipe segment.

2. The method of claim 1, wherein determining a predicted parameter based on the received pipe segment criteria for the pipe segment comprises determining a suggested frequency range at which to measure the actual speed of sound.

3. The method of claim 2, wherein determining the suggested frequency range comprises the steps of:
   determining a magnitude of an explicit frequency that varies with a diameter of the pipe segment and a distance between the first computing node and the second computing node;
   determining a lower range value equal to the explicit frequency multiplied by a first empirical parameter; and
   determining an upper range value equal to the explicit frequency multiplied by a second empirical parameter.

4. The method of claim 1, wherein calculation of the theoretical speed of sound in the pipe segment is based on the pipe segment criteria.

5. The method of claim 1, wherein measuring the actual speed of sound comprises the steps of:
   implementing a noise source at a predetermined location;
   measuring a propagation time delay between signals observed at the first computing node and the second computing node; and
   calculating the actual speed of sound in the pipe segment based on the length of the pipe segment and the propagation time delay.

6. The method of claim 1, wherein the pipe segment criteria comprises pipe characteristics, water characteristics, and the length of the pipe.

7. The method of claim 6, wherein the pipe characteristics comprises a young modulus, an inner diameter, a wall thickness, and a lining thickness.

8. The method of claim 6, wherein the water characteristics comprises a bulk modulus, a temperature, a background pressure, and a background velocity.

9. A system for collecting and analyzing acoustic data for condition assessment within a fluid distribution system, comprising:
   a plurality of computing nodes in communication with the fluid distribution system and configured to acquire acoustic data in the fluid distribution system; and
   a computing host in communication with the plurality of computing nodes, the computing host programmed to perform steps comprising
     receiving pipe segment criteria for a pipe segment, the pipe segment comprising a length of a pipe between a first computing node and a second computing node of the plurality of computing nodes,
     determining a predicted parameter based on the received pipe segment criteria for the pipe segment,
     utilizing the predicted parameter to measure an actual speed of sound for the pipe segment between the first computing node and the second computing node, and
     comparing the actual speed of sound and a theoretical speed of sound to calculate a predicted pipe degradation for the pipe segment.

10. The system of claim 9, wherein determining a predicted parameter based on the received pipe segment criteria for the pipe segment comprises determining a suggested frequency range at which to measure the actual speed of sound, comprising the steps of:
    determining a magnitude of an explicit frequency that varies with a diameter of the pipe segment and a distance between the first computing node and the second computing node;
    determining a lower range value equal to the explicit frequency multiplied by a first empirical parameter; and
    determining an upper range value equal to the explicit frequency multiplied by a second empirical parameter.

11. The system of claim 10, wherein the actual speed of sound between the first computing node and the second computing node is determined based on the suggested frequency range.

12. The system of claim 9, wherein the calculation of the theoretical speed of sound in the pipe segment is based on the pipe segment criteria.

13. The system of claim 9, wherein measuring the actual speed of sound comprises the steps of:
    implementing a noise source at a predetermined location;
    measuring a propagation time delay between signals observed at the first computing node and the second computing node; and
    calculating the actual speed of sound in the pipe segment based on the length of the pipe segment and the propagation time delay.

14. The system of claim 9, wherein the pipe segment criteria comprises pipe characteristics, water characteristics, and the length of the pipe.

15. The system of claim 14, wherein the pipe characteristics comprises a young modulus, an inner diameter, a wall thickness, and a lining thickness.

16. The system of claim 14, wherein the water characteristics comprises a bulk modulus, a temperature, a background pressure, and a background velocity.

17. A non-transitory computer-readable storage medium storing instructions that, when executed by a processing resource, cause the processing resource to perform steps comprising:
    receiving pipe segment criteria for a pipe segment, the pipe segment comprising a length of a pipe between a first computing node and a second computing node;

determining a predicted parameter based on the received pipe segment criteria for the pipe segment;

utilizing the predicted parameter to measure an actual speed of sound for the pipe segment between the first computing node and the second computing node; and comparing the actual speed of sound and a theoretical speed of sound to calculate a predicted pipe degradation for the pipe segment.

18. The non-transitory computer-readable storage medium of claim 17, wherein determining a predicted parameter based on the received pipe segment criteria for the pipe segment comprises determining a suggested frequency range at which to measure the actual speed of sound, comprising the steps of:

determining a magnitude of an explicit frequency that varies with a diameter of the pipe segment and a distance between the first computing node and the second computing node;

determining a lower range value equal to the explicit frequency multiplied by a first empirical parameter; and determining an upper range value equal to the explicit frequency multiplied by a second empirical parameter.

19. The non-transitory computer-readable storage medium of claim 18, wherein the actual speed of sound between the first computing node and the second computing node is determined based on the suggested frequency range.

20. The non-transitory computer-readable storage medium of claim 17, wherein the calculation of the theoretical speed of sound in the pipe segment is based on the pipe segment criteria.

* * * * *